United States Patent
Wells et al.

(10) Patent No.: US 9,522,931 B2
(45) Date of Patent: Dec. 20, 2016

(54) PROCESS FOR THE PREPARATION OF COMPOUNDS USEFUL AS INHIBITORS OF SGLT-2

(75) Inventors: Kenneth M. Wells, Doylestown, PA (US); Ronald K. Russell, Titusville, NJ (US); Xun Li, New Hope, PA (US); Shawn Branum, Easton, PA (US); Derek A. Beauchamp, Schwenksville, PA (US); Sumihiro Nomura, Osaka (JP); Yosuke Matsumura, Osaka (JP)

(73) Assignee: Janssen Pharmaceutica NV, Beerse (BE)

( * ) Notice: Subject to any disclaimer, the term of this patent is extended or adjusted under 35 U.S.C. 154(b) by 162 days.

(21) Appl. No.: 14/118,643

(22) PCT Filed: May 18, 2012

(86) PCT No.: PCT/US2012/038481
§ 371 (c)(1),
(2), (4) Date: Apr. 3, 2014

(87) PCT Pub. No.: WO2012/162115
PCT Pub. Date: Nov. 29, 2012

(65) Prior Publication Data
US 2014/0206858 A1  Jul. 24, 2014

Related U.S. Application Data

(60) Provisional application No. 61/488,184, filed on May 20, 2011.

(51) Int. Cl.
*C07H 19/044* (2006.01)
*C07D 407/04* (2006.01)

(52) U.S. Cl.
CPC ........... *C07H 19/044* (2013.01); *C07D 407/04* (2013.01)

(58) Field of Classification Search
CPC ............................ C07D 407/04; C07H 19/044
USPC ........................................................ 536/28.6
See application file for complete search history.

(56) References Cited

U.S. PATENT DOCUMENTS

| | | | | |
|---|---|---|---|---|
| 4,792,568 A | * | 12/1988 | Auerbach | C07D 207/333 514/423 |
| 5,707,989 A | | 1/1998 | Himmelsbach | |
| 6,462,192 B2 | * | 10/2002 | Robinson | A61K 41/0071 534/10 |
| 2005/0233988 A1 | | 10/2005 | Nomura et al. | |
| 2006/0122126 A1 | | 6/2006 | Imamura et al. | |
| 2008/0027014 A1 | | 1/2008 | Nomura et al. | |

FOREIGN PATENT DOCUMENTS

| | | |
|---|---|---|
| JP | 2008-050353 A | 3/2008 |
| JP | 2008-528441 A | 7/2008 |
| JP | 2009-196984 A | 9/2009 |
| JP | 2009-196985 A | 9/2009 |
| JP | 2009-544572 | 9/2009 |
| WO | WO 2004/080990 A1 | 9/2004 |
| WO | WO 2006/080577 A1 | 8/2006 |
| WO | WO 2008/013322 A1 * | 1/2008 ............. C07H 19/04 |
| WO | WO 2011/048148 A2 | 4/2011 |

OTHER PUBLICATIONS

International Search Report relating to International Patent Application No. PCT/US2012/038481, filed May 18, 2012. Date of Mailing of International Search Report: Jan. 23, 2013.
Writtin Opinion of the International Searching Authority relating to International Patent Application No. PCT/US2012/038481, May 18, 2012. Date of Mailing of Written Opinion: Jan. 23, 2013.
Unger, R.H., et al., "Hyperglycemia as an inducer as well as a consequence of impaired islet cell function and insulin resistance: implication for the management of diabetes", *Diabetologia*, 1985, vol. 28, pp. 119-121.
Rossetti, L., et al., "Glucose Toxicity", *Diabetes Care*, 1990, vol. 13, No. 6, pp. 610-630.
Rossetti, L., et al., "Correction of Hyperglycemia with Phlorizin Normalizes Tissue sensitivity to Insulin in Diabetic Rats", *J. Clin. Invest.*, 1987, vol. 79, pp. 1510-1515.
Rossetti, L., et al., "Effect of Chronic Hyperglycemia on in Vivo Insulin Secretion in Partially Pancreatectomized Rats", *J. Clin Invest.*, 1987, vol. 80, pp. 1037-1044.
Kahn, B.B., et al., "Normalization of blood glucose in diabetic rats with phlorizin treatment reverses insulin-resistant glucose transport in adipose cells without restoring glucose transporter gene expression", *J. Clin. Invest.*, 1991, vol. 87, pp. 561-570.
Tsujihara, K., et al., "Na+-Glucose Cotransporter (SGLT) Inhibitors as Antidiabetic Agents. 4. Synthesis and Pharmacological Properties of 4'-Dehydroxyphlorizin Derivatives Substituted on the B Ring", *J. Med. Chem.*, 1999, vol. 42, pp. 5311-5324.
Arakawa, K., et al., Improved diabetic syndrome in C57BL/Ks-db/db mice by oral administration of the Na+-glucose cotransporter inhibitor T-1095, *Br. J. Pharmacol.*, 2001, vol. 132, pp. 578-586.
Ueta, K., et al., "Long-term treatment with the Na+-glucose cotransporter inhibitor T-1095 causes sustained improvement in hyperglycemia and prevents diabetic neuropathy in Goto-kakizaki Rats", *Life Sciences*, 2005, vol. 76, pp. 2655-2668.
Levin, R.Y., et al., "Bromination and acylatin of phenylcyclopropane", *Zhurmal Obshchei Khimii*, (1961), pp. 3480-3481, vol. 31.

* cited by examiner

*Primary Examiner* — Ganapathy Krishnan

(57) ABSTRACT

The present invention is directed to a novel process for the preparation of compounds having inhibitory activity against sodium-dependent glucose transporter (SGLT) being present in the intestine or kidney.

20 Claims, 2 Drawing Sheets pXRD Crystalline Ethanolate of Compound of Formula (I-T)

pXRD Crystalline Hemihydrate of Compound of Formula (I-T)

PROCESS FOR THE PREPARATION OF COMPOUNDS USEFUL AS INHIBITORS OF SGLT-2

This application is a national stage of Application No. PCT/US2012/038481, filed May 18, 2012, which claims the benefit of U.S. Provisional Application 61/488,184, filed on May 20, 2011, which is incorporated by reference herein in its entirety.

FIELD OF THE INVENTION

The present invention is directed to a novel process for the preparation of compounds having inhibitory activity against sodium-dependent glucose transporter (SGLT) being present in the intestine or kidney.

BACKGROUND OF THE INVENTION

Diet therapy and exercise therapy are essential in the treatment of diabetes mellitus. When these therapies do not sufficiently control the conditions of patients, insulin or an oral antidiabetic agent is additionally used for the treatment of diabetes. At the present, there have been used as an antidiabetic agent biguanide compounds, sulfonylurea compounds, insulin resistance improving agents and α-glucosidase inhibitors. However, these antidiabetic agents have various side effects. For example, biguanide compounds cause lactic acidosis, sulfonylurea compounds cause significant hypoglycemia, insulin resistance improving agents cause edema and heart failure, and α-glucosidase inhibitors cause abdominal bloating and diarrhea. Under such circumstances, it has been desired to develop novel drugs for treatment of diabetes mellitus having no such side effects.

Recently, it has been reported that hyperglycemia participates in the onset and progressive impairment of diabetes mellitus, i.e., glucose toxicity theory. Namely, chronic hyperglycemia leads to decrease of insulin secretion and further to decrease of insulin sensitivity, and as a result, the blood glucose concentration is increased so that diabetes mellitus is self-exacerbated [Unger, R. H., et al., "Hyperglycemia as an inducer as well as a consequence of impaired islet cell function and insulin resistance: implication for the management of diabetes", *Diabetoloaia*, 1985, vol. 28, pp 119-121; Rossetti, L., et al., "Glucose Toxicity", *Diabetes Care*, 1990, vol. 13, no. 6, pp 610-630]. Therefore, by treating hyperglycemia, the aforementioned self-exacerbating cycle is interrupted so that the prophylaxis or treatment of diabetes mellitus is made possible.

As one of the methods for treating hyperglycemia, it is considered to excrete an excess amount of glucose directly into urine so that the blood glucose concentration is normalized. For example, by inhibiting sodium-dependent glucose transporter being present at the proximal convoluted tubule of kidney, the re-absorption of glucose at the kidney is inhibited, by which the excretion of glucose into urine is promoted so that the blood glucose level is decreased. In fact, it is confirmed that by continuous subcutaneous administration of phlorizin having SGLT inhibitory activity to diabetic animal models, hyperglycemia is normalized and the blood glucose level thereof can be kept normal for a long time so that the insulin secretion and insulin resistance are improved [Rossetti, L., et al., "Correction of Hyperglycemia with Phlorizin Normalizes Tissue sensitivity to Insulin in Diabetic Rats", *J. Clin. Invest.* 1987, vol. 79, pp 1510-1515; Rossetti, L., et al., "Effect of Chronic Hyperglycemia on in Vivo Insulin Secretion in Partially Pancreatectomized Rats", *J. Clin Invest.* 1987, vol. 80, pp 1037-1044; Kahn, B. B., et al., "Normalization of blood glucose in diabetic rats with phlorizin treatment reverses insulin-resistant glucose transport in adipose cells without restoring glucose transporter gene expression", *J. Clin. Invest.*, 1991, vol. 87, pp 561-570]

In addition, by treating diabetic animal models with SGLT inhibitory agents for a long time, insulin secretion response and insulin sensitivity of the animals are improved without incurring any adverse affects on the kidney or imbalance in blood levels of electrolytes, and as a result, the onset and progress of diabetic nephropathy and diabetic neuropathy are prevented [Tsujihara, K., et al., "Na+-Glucose Cotransporter (SGLT) Inhibitors as Antidiabetic Agents. 4. Synthesis and Pharmacological Properties of 4'-Dehydroxyphlorizin Derivatives Substituted on the B Ring", *J. Med. Chem.* 1999, vol. 42, pp 5311-5324; Arakawa, K., et al., "Improved diabetic syndrome in C57BL/Ks-db/db mice by oral administration of the Na+-glucose cotransporter inhibitor T-1095, *Br. J. Pharmacol.*, 2001, vol. 132, pp 578-586; Ueta, K., et al., "Long-term treatment with the Na+-glucose cotransporter inhibitor T-1095 causes sustained improvement in hyperglycemia and prevents diabetic neuropathy in Goto-kakizaki Rats", *Life Sciences*, 2005, vol. 76, pp 2655-2668].

From the above, SGLT inhibitors may be expected to improve insulin secretion and insulin resistance by decreasing the blood glucose level in diabetic patients and further prevent the onset and progress of diabetes mellitus and diabetic complications.

SUMMARY OF THE INVENTION

The present invention is directed to a process for the preparation of a compound of formula (I)

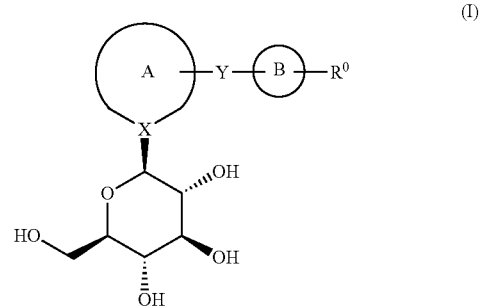

wherein Ring A and Ring B are one of the following:
(1) Ring A is an optionally substituted unsaturated monocyclic heterocyclic ring, and Ring B is an optionally substituted unsaturated monocyclic heterocyclic ring, an optionally substituted unsaturated fused heterobicyclic ring, or an optionally substituted benzene ring;
(2) Ring A is an optionally substituted benzene ring, and Ring B is an optionally substituted unsaturated monocyclic heterocyclic ring, or an optionally substituted unsaturated fused heterobicyclic ring wherein Y is linked to the heterocyclic ring of the fused heterobicyclic ring; or
(3) Ring A is an optionally substituted unsaturated fused heterobicyclic ring, wherein the sugar moiety X-(sugar) and the moiety —Y-(Ring B) are both on the same heterocyclic ring of the fused heterobicyclic ring, and Ring B is an optionally substituted unsaturated monocyclic heterocyclic ring, an optionally substituted unsaturated fused heterobicyclic ring, or an optionally substituted benzene ring;
provided that Y is bound to an aromatic carbon atom on Ring A;

X is a carbon atom or a nitrogen atom;
Y is —CH$_2$—;
R$^0$ is selected from the group consisting of optionally substituted cyclopropyl, optionally substituted aryl, optionally substituted unsaturated monocyclic heterocyclic ring, optionally substituted unsaturated fused heterobicyclic ring and optionally substituted cycloalkenyl;
or a pharmaceutically acceptable salt or prodrug thereof; comprising

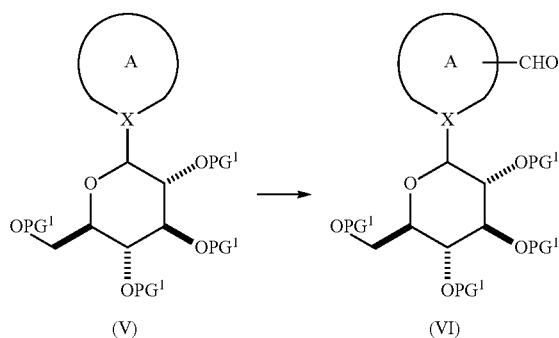

(V)     (VI)

reacting a compound of formula (V), wherein PG$^1$ is an oxygen protecting group with an acylating reagent; wherein the acylating reagent is present in an amount in the range of from about 1.5 to about 3.0 molar equivalents; in the presence of a carbonyl source; in a first organic solvent; at a temperature in the range of from about room temperature to about 40° C.; to yield the corresponding compound of formula (VI);

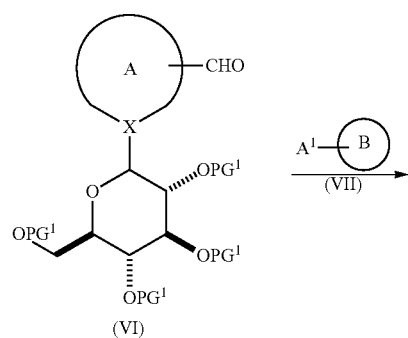

(VI)

(VIII)

reacting the compound of formula (VI) with a compound of formula (VII), wherein A$^1$ is MgBr or MgCl; in an anhydrous organic solvent; to yield the corresponding compound of formula (VIII);

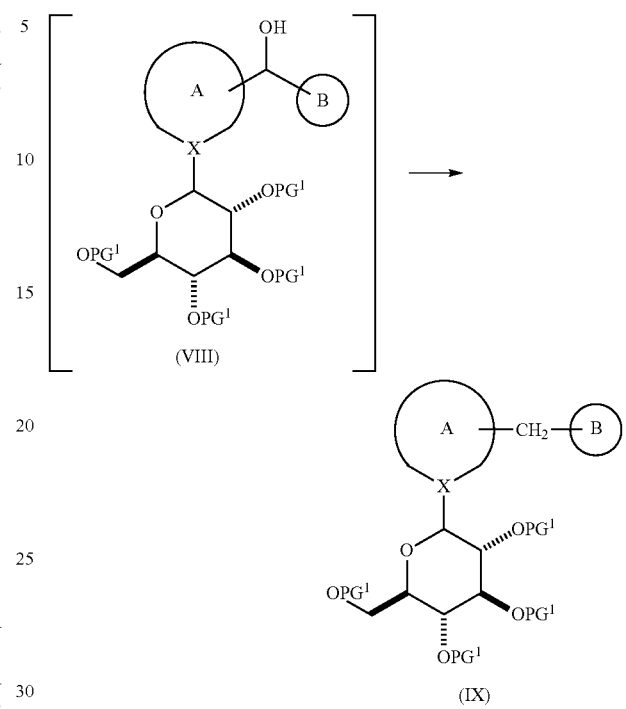

(VIII)

(IX)

reacting the compound of formula (VIII) with a reducing agent; in the presence of a Lewis acid; in a second organic solvent; to yield the corresponding compound of formula (IX);

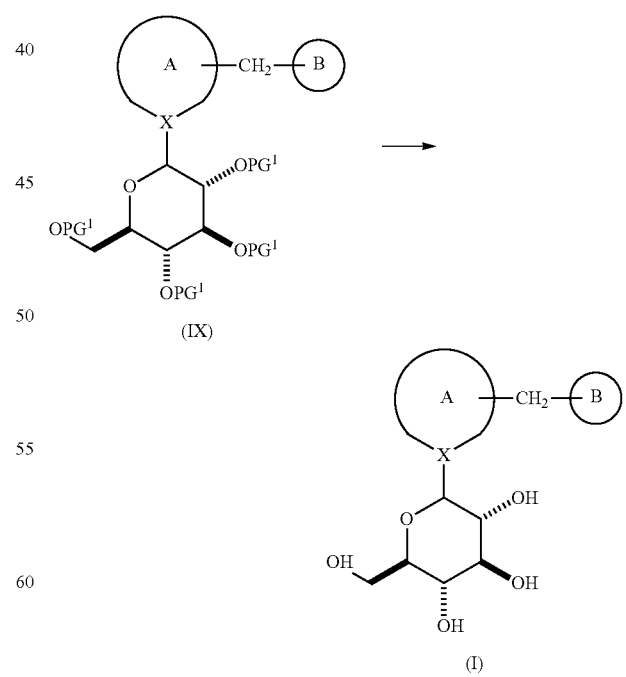

(IX)

(I)

de-protecting the compound of formula (IX); to yield the corresponding compound of formula (I).

The present invention is further directed to a process for the preparation of a compound of formula (I-S)

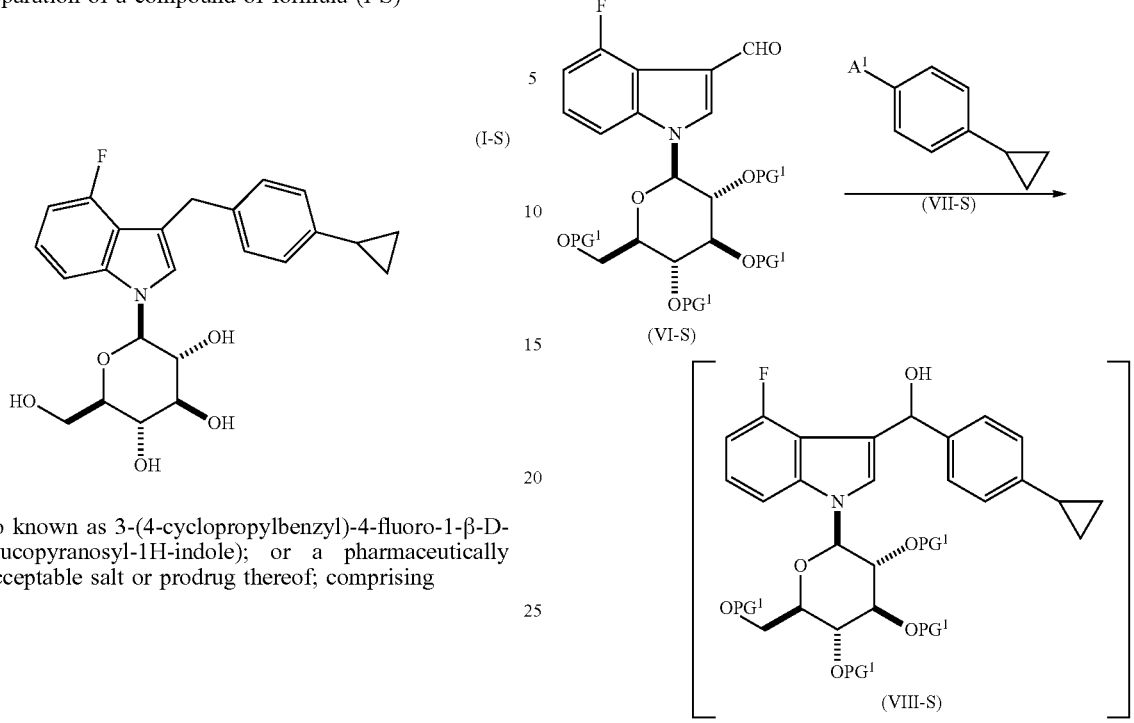

(also known as 3-(4-cyclopropylbenzyl)-4-fluoro-1-β-D-glucopyranosyl-1H-indole); or a pharmaceutically acceptable salt or prodrug thereof; comprising

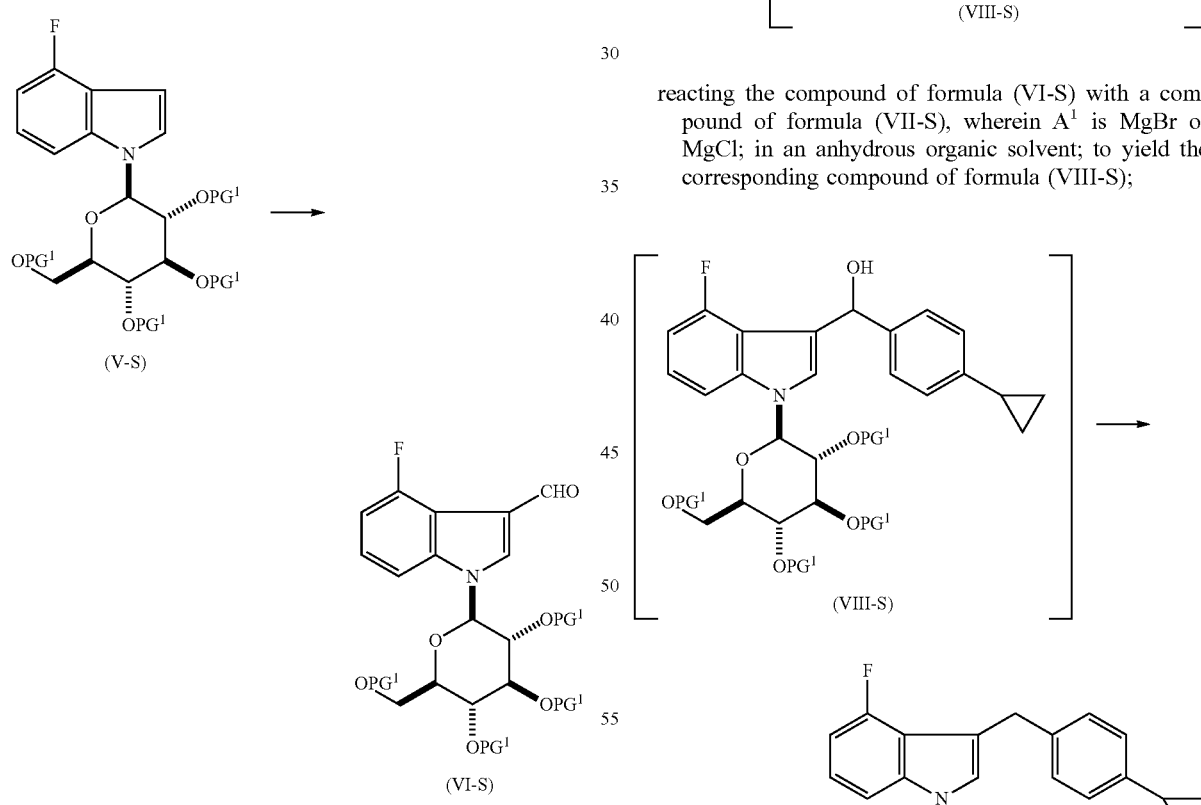

reacting a compound of formula (V-S), wherein $PG^1$ is an oxygen protecting group with an acylating reagent; wherein the acylating reagent is present in an amount in the range of from about 1.5 to about 3.0 molar equivalents; in the presence of a carbonyl source; in a first organic solvent; at a temperature in the range of from about room temperature to about 40° C.; to yield the corresponding compound of formula (VI-S);

reacting the compound of formula (VI-S) with a compound of formula (VII-S), wherein $A^1$ is MgBr or MgCl; in an anhydrous organic solvent; to yield the corresponding compound of formula (VIII-S);

reacting the compound of formula (VIII-S) with a reducing agent in the presence of a Lewis acid; in a second organic solvent; to yield the corresponding compound of formula (IX-S);

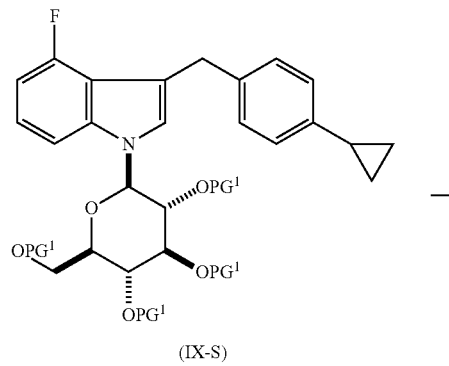

(IX-S)

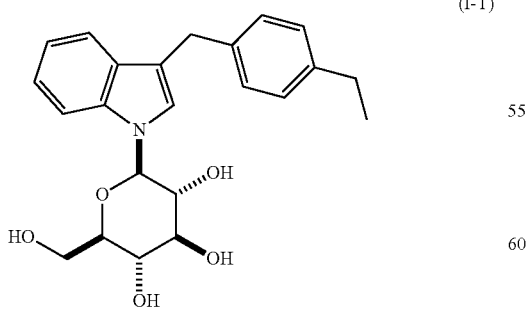

(I-S)

de-protecting the compound of formula (IX-S); to yield the corresponding compound of formula (I-S).

The present invention is further directed to a process for the preparation of a compound of formula (I-T)

(I-T)

(also known as 3-(4-ethyl-benzyl)-1-β-D-glucopyranosyl-1H-indole); or a pharmaceutically acceptable salt or prodrug thereof; comprising

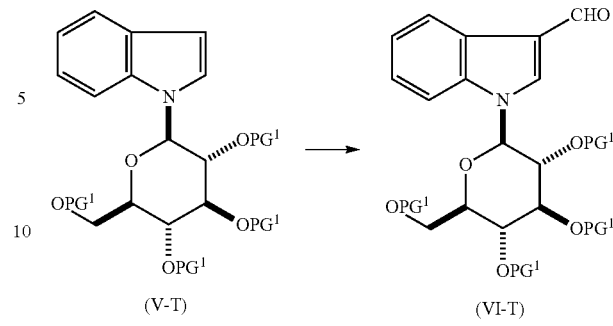

reacting a compound of formula (V-T), wherein $PG^1$ is an oxygen protecting group with an acylating reagent; wherein the acylating reagent is present in an amount in the range of from about 1.5 to about 3.0 molar equivalents; in the presence of a carbonyl source; in a first organic solvent; at a temperature in the range of from about room temperature to about 40° C.; to yield the corresponding compound of formula (VI-T);

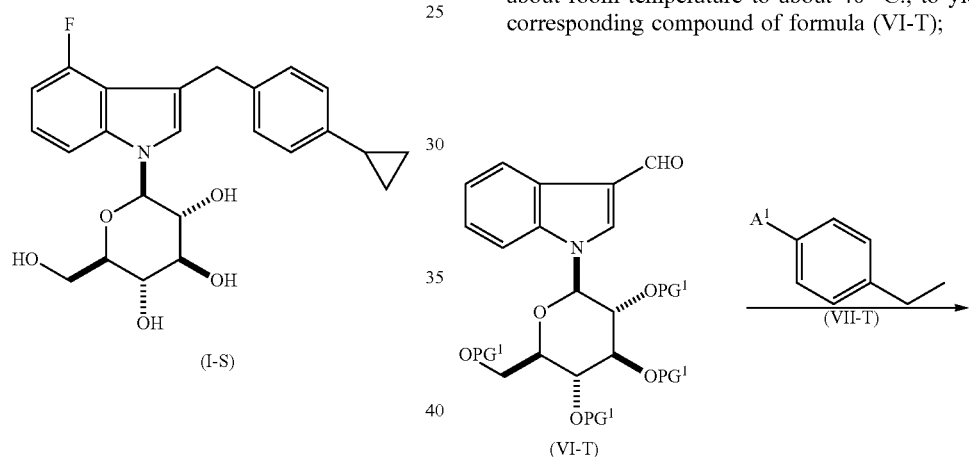

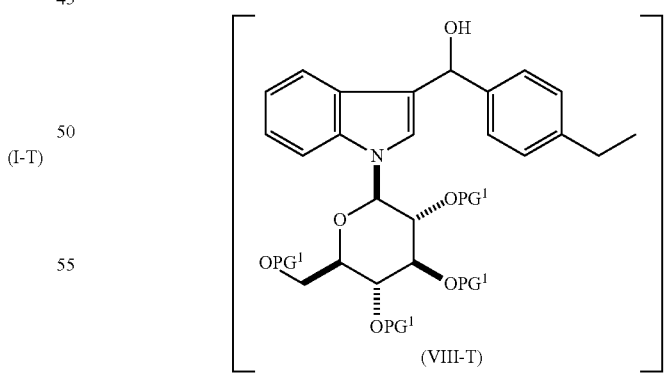

reacting the compound of formula (VI-T) with a compound of formula (VII-T), wherein $A^1$ is MgBr or MgCl; in an anhydrous organic solvent; to yield the corresponding compound of formula (VIII-T);

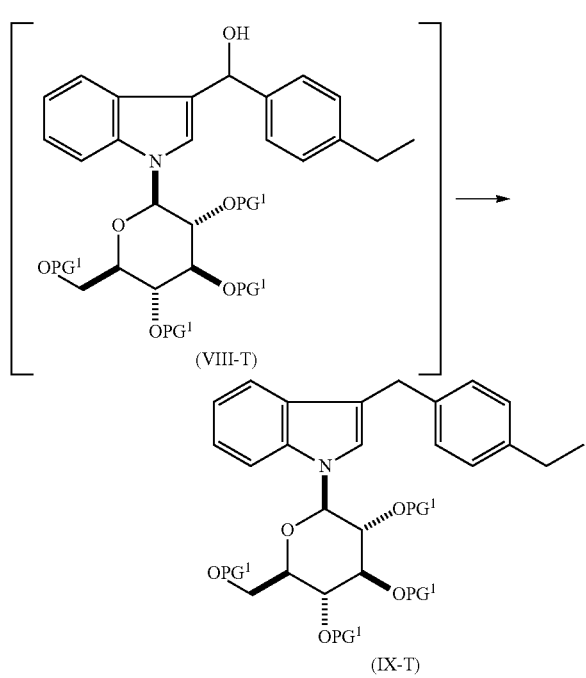

(VIII-T)

(IX-T)

reacting the compound of formula (VIII-T) with a reducing agent; in the presence of a Lewis acid; in a second organic solvent; to yield the corresponding compound of formula (IX-T);

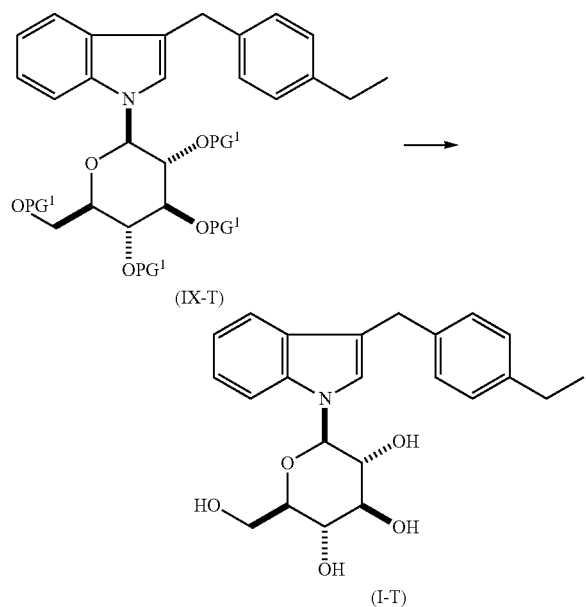

(IX-T)

(I-T)

de-protecting the compound of formula (IX-T); to yield the corresponding compound of formula (I-T).

The present invention is further directed to a crystalline ethanol solvate form of the compound of formula (I-S). The present invention is further directed to a crystalline hemihydrate form of the compound of formula (I-S).

The present invention is further directed to a crystalline ethanol solvate form of the compound of formula (I-T). The present invention is further directed to a crystalline hemihydrate form of the compound of formula (I-T).

The present invention is further directed to an improved process for the preparation of a compound of formula (C)

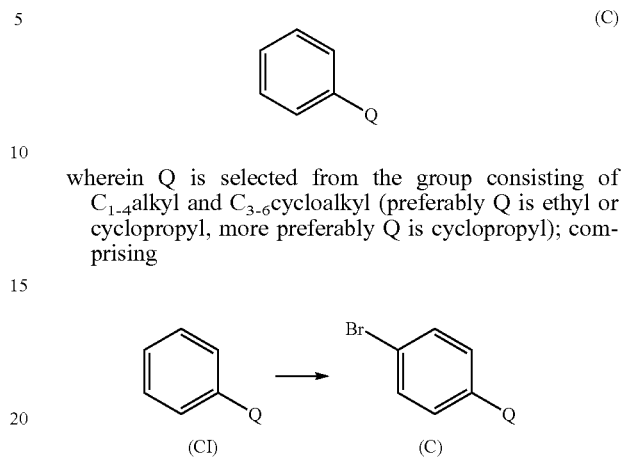

(C)

wherein Q is selected from the group consisting of $C_{1-4}$alkyl and $C_{3-6}$cycloalkyl (preferably Q is ethyl or cyclopropyl, more preferably Q is cyclopropyl); comprising (CI)   (C)

reacting a compound of formula (CI) with a source of bromine; in an organic solvent with a freezing point lower than about −78° C. (preferably DCM); at a temperature in the range of from about −65° C. to about −78° C.; to yield the corresponding compound of formula (C).

The present invention is further directed to a product prepared according to any of the processes described herein. Illustrative of the invention is a pharmaceutical composition comprising a pharmaceutically acceptable carrier and the product prepared according to any of the processes described herein. An illustration of the invention is a pharmaceutical composition made by mixing the product prepared according to any of the processes described herein and a pharmaceutically acceptable carrier. Illustrating the invention is a process for making a pharmaceutical composition comprising mixing the product prepared according to any of the processes described herein and a pharmaceutically acceptable carrier.

Exemplifying the invention are methods of treating a disorder mediated by SGLT (including treating or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension) comprising administering to the subject in need thereof a therapeutically effective amount of any of the compounds or pharmaceutical compositions described above.

Further exemplifying the invention are methods of treating type 1 and type 2 diabetes mellitus, comprising administering to a subject in need of treatment a therapeutically effective amount of a therapeutically effective amount of any of the compounds or pharmaceutical compositions described above, alone or in combination with at least one antidiabetic agent, agent for treating diabetic complications, anti-obesity agent, antihypertensive agent, antiplatelet agent, anti-atherosclerotic agent and/or hypolipidemic agent.

DETAILED DESCRIPTION OF THE INVENTION

Figure 1:
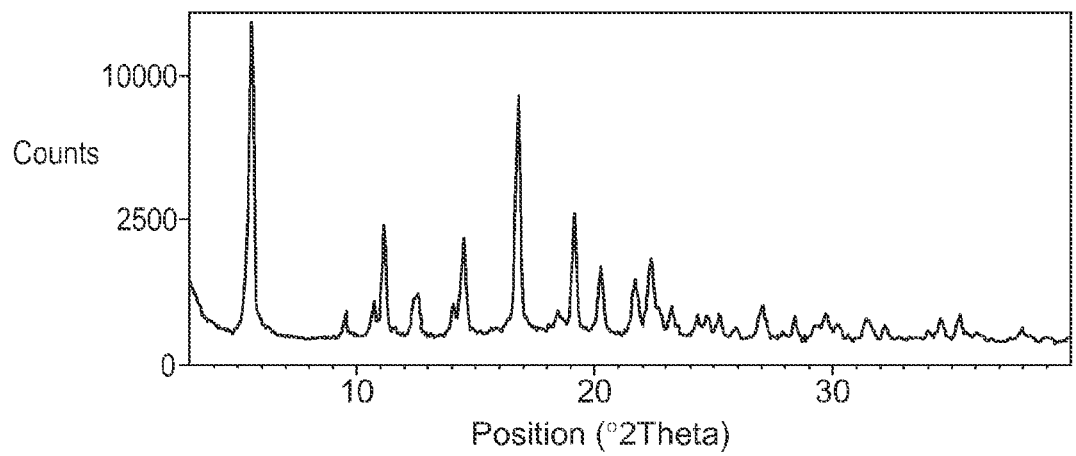
FIG. 1 illustrates a representative pXRD for the crystalline ethanolate of the compound of formula (I-S).

The present invention is directed to a process for the preparation of compounds of formula (I)

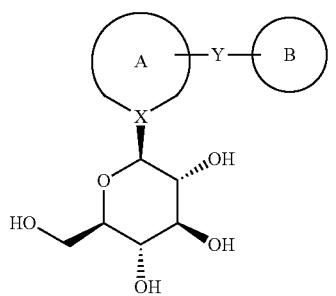

(I)

wherein X, Y, Ring A and Ring B are as herein defined; and pharmaceutically acceptable salts thereof. The process of the present invention (as detailed in Schemes 1-3 which follow herein) comprises an acylation reaction step (also known as a Vilsmeier reaction). It has unexpectedly been found that by limiting the acylating reagent to an amount in the range of from about 1.5 to about 3.0 molar equivalents; and further, by running the acylating reaction step at a temperature in the range of from about room temperature to about 40° C.; the reaction is controlled to significantly reduce the amount of (undesired) bi-acylation product that is produced, and to significantly increase the yield of the desired mono-acylated product. The improved yield of the mono-acylated product makes the process of the present invention particularly advantageous for large scale manufacture of the compounds of formula (I).

The compounds of the formula (I) exhibit inhibitory activity against sodium-dependent glucose transporter being present in the intestine and the kidney of mammalian species, and is useful in the treatment of diabetes mellitus or diabetic complications such as diabetic retinopathy, diabetic neuropathy, diabetic nephropathy, obesity, and delayed wound healing. In an embodiment, the present invention is directed to a process for the preparation of the compound of formula (I-S) or a pharmaceutically acceptable salt thereof. In another embodiment, the present invention is directed to a process for the preparation of the compound of formula (I-T) or a pharmaceutically acceptable salt thereof.

Examples of the optionally substituted unsaturated monocyclic heterocyclic ring of the present invention include an unsaturated monocyclic heterocyclic ring which may optionally be substituted by 1-5 substituents selected from the group consisting of a halogen atom, a cyano group, an oxo group, a hydroxyl group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, and a heterocyclylsulfonyl group wherein each substituent may optionally be further substituted by these substituents.

Examples of the optionally substituted unsaturated fused heterobicyclic ring of the present invention include an unsaturated fused heterobicyclic ring which may optionally be substituted by 1-5 substituents selected from the group consisting of a halogen atom, a cyano group, an oxo group, a hydroxy group, a mercapto group, a carboxyl group, a sulfo group, an alkyl group, an alkenyl group, an alkynyl group, a cycloalkyl group, a cycloalkylidene-methyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynyl-carbonyl group, an arylcarbonyl group, a heterocyclylcarbonyl group, an alkoxycarbonyl group, an alkenyloxycarbonyl group, an alkynyloxy-carbonyl group, a cycloalkyloxycarbonyl group, a cycloalkenyloxy-carbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoyl-amino group, a mono- or di-alkoxycarbonylamino group, a mono- or di-arylcarbonylamino group, an alkylsulfinylamino group, an alkyl-sulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cyclo-alkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, and a heterocyclylsulfonyl group, wherein each substituent may optionally be further substituted by these substituents.

Examples of the optionally substituted benzene ring of the present invention include a benzene ring which may optionally be substituted by 1-5 substituents selected from the group consisting of a halogen atom, a cyano group, a hydroxy group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, a heterocyclylsulfonyl group, an alkylene group, an alkyleneoxy group, an alkylenedioxy group, and an alkenylene group wherein each substituent may optionally be further substituted by these substituents. Moreover, examples of the optionally substituted benzene ring include a benzene ring substituted with an alkylene group to form an annelated carbocycle together with the carbon atoms to which they are attached, and also includes a benzene ring substituted with an alkenylene group to form an annelated carbocycle such as a fused benzene ring together with the carbon atoms to which they are attached.

Preferable examples of the optionally substituted unsaturated monocyclic heterocyclic ring include an unsaturated monocyclic heterocyclic ring which may optionally be substituted by 1-3 substituents selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, and an oxo group.

Preferable examples of the optionally substituted unsaturated fused heterobicyclic ring include an unsaturated fused heterobicyclic ring which may optionally be substituted by 1-3 substituents independently selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, and an oxo group.

Preferable examples of the optionally substituted benzene ring include a benzene ring which may optionally be substituted by 1-3 substituents selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, an alkylene group, an alkyleneoxy group, an alkylenedioxy group, and an alkenylene group.

In another preferable embodiment of the present invention, the optionally substituted unsaturated monocyclic heterocyclic ring is an unsaturated monocyclic heterocyclic ring which may optionally be substituted by 1-3 substituents, independently selected from the group consisting of a halogen atom, a hydroxy group, a cyano group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, an alkanoylamino group, an alkoxycarbonylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group;

the optionally substituted unsaturated fused heterobicyclic ring is an unsaturated fused heterobicyclic ring which may optionally be substituted by 1-3 substituents selected from the group consisting of a halogen atom, a hydroxy group, a cyano group, an alkyl group, an alkenyl group, an alkynyl group, a cycloalkyl group, a cycloalkylidenemethyl group, an alkoxy group, an alkylthio group, an alkylsulfonyl group, an alkylsulfinyl group, an amino group, a mono- or di-alkylamino group, an alkanoylamino group, an alkoxycarbonylamino group, a sulfamoyl group, a mono- or di-alkyl-sulfamoyl group, a carboxyl group, an alkoxycarbonyl group, a carbamoyl group, a mono- or di-alkylcarbamoyl group, an alkanoyl group, an alkylsulfonylamino group, a phenyl group, a phenoxy group, a phenylsulfonylamino group, phenylsulfonyl group, a heterocyclyl group, and an oxo group; and the optionally substituted benzene ring is a benzene ring which may optionally be substituted by 1-3 substituents, independently selected from the group consisting of a halogen atom, a hydroxy group, a cyano group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, an alkanoylamino group, an alkoxycarbonylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group, and an alkenylene group;

wherein each of the above-mentioned substituents on the unsaturated monocyclic heterocyclic ring, the unsaturated fused heterobicyclic ring and the benzene ring may further be substituted by 1-3 substituents, independently selected from the group consisting of a halogen atom, a hydroxy group, a cyano group, an alkyl group, a haloalkyl group, an alkoxy group, a haloalkoxy group, an alkanoyl group, an alkylthio group, an alkylsulfonyl group, a mono- or di-alkylamino group, a carboxyl group, an alkoxycarbonyl group, a phenyl group, an alkyleneoxy group, an alkylenedioxy group, an oxo group, a carbamoyl group, and a mono- or di-alkylcarbamoyl group.

In a preferable embodiment, the optionally substituted unsaturated monocyclic heterocyclic ring is an unsaturated monocyclic heterocyclic ring which may optionally be substituted by 1-3 substituents, independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxyl group, an alkoxycarbonyl group, a carbamoyl group, a mono- or di-alkylcarbamoyl group, a phenyl group, a heterocyclyl group, and an oxo group;

the optionally substituted unsaturated fused heterobicyclic ring is an unsaturated fused heterobicyclic ring which may optionally be substituted by 1-3 substituents independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxy group, an alkoxycarbonyl group, a carbamoyl group, a mono- or di-alkylcarbamoyl group, a phenyl group, a heterocyclyl group, and an oxo group; and the optionally substituted benzene ring is a benzene ring which may optionally be substituted by 1-3 substituents, independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxyl group, an alkoxycarbonyl group, a carbamoyl group, a mono- or di-alkylcarbamoyl group, a phenyl group, a heterocyclyl group, an alkylene group, and an alkenylene group;

wherein each of the above-mentioned substituents on the unsaturated monocyclic heterocyclic ring, the unsaturated fused heterobicyclic ring and the benzene ring may further be substituted by 1-3 substituents, independently selected from the group consisting of a halogen atom, a cyano group, an alkyl group, a haloalkyl group, an alkoxy group, a haloalkoxy group, an alkanoyl group, a mono- or di-alkylamino group, a carboxyl group, a hydroxy group, a phenyl group, an alkylenedioxy group, an alkyleneoxy group, an alkoxycarbonyl group, a carbamoyl group and a mono- or di-alkylcarbamoyl group.

In another preferable embodiment, (1) Ring A is an unsaturated monocyclic heterocyclic ring which may optionally be substituted by 1-3 substituents, independently selected from the group consisting of a halogen atom, a hydroxy group, a cyano group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group, and Ring B is an unsaturated monocyclic heterocyclic ring, an unsaturated fused heterobicyclic ring, or a benzene ring, each of which may optionally be substituted by 1-3 substituents, independently selected from the group consisting of a halogen atom, a hydroxy group, a cyano group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group, and an alkenylene group;

(2) Ring A is a benzene ring which may optionally be substituted by 1-3 substituents, independently selected from the group consisting of a halogen atom, a hydroxy group, a cyano group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, an alkanoylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group, and an alkenylene group, and Ring B is an unsaturated monocyclic heterocyclic ring or an unsaturated fused heterobicyclic ring, each of which may optionally be substituted by 1-3 substituents, independently selected from the group consisting of a halogen atom, a hydroxy group, a cyano group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group and an oxo group; or (3) Ring A is an unsaturated fused heterobicyclic ring which may optionally be substituted by 1-3 substituents, independently selected from the group consisting of a halogen atom, a hydroxy group, a cyano group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group, and Ring B is an unsaturated monocyclic heterocyclic ring, an unsaturated fused heterobicyclic ring, or a benzene ring, each of which may optionally be substituted by 1-3 substituents, independently selected from the group consisting of a halogen atom, a hydroxy group, a cyano group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group and an oxo group;

wherein each of the above-mentioned substituents on Ring A and Ring B may optionally be substituted by 1-3 substituents, independently selected from the group consisting of a halogen atom, a cyano group, an alkyl group, a haloalkyl group, an alkoxy group, a haloalkoxy group, an alkanoyl group, a mono- or di-alkylamino group, a carboxyl group, a hydroxy group, a phenyl group, an alkylenedioxy group, an alkyleneoxy group, an alkoxycarbonyl group, a carbamoyl group and a mono- or di-alkylcarbamoyl group.

In a more preferable embodiment of the present invention, Ring A and Ring B are:

(1) Ring A is an unsaturated monocyclic heterocyclic ring which may optionally be substituted by a halogen atom, a lower alkyl group, a halo-lower alkyl group, a lower alkoxy group, or an oxo group, and Ring B is (a) a benzene ring which may optionally be substituted by a halogen atom; a cyano group; a lower alkyl group; a halo-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, or a mono- or di-lower alkylamino group; or a heterocyclyl group optionally substituted by a halogen atom, a cyano group, a lower alkyl group, a halo-lower alkyl group, a lower alkoxy group, or a mono- or di-lower alkylamino group; (b) an unsaturated monocyclic heterocyclic ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; or (c) an unsaturated fused heterobicyclic ring which may optionally be substituted by a group selected from a halogen atom, cyano group, a lower alkyl group, a halo-lower alkyl group, a lower alkoxy group, a halo-lower alkoxy group, a mono- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group;

(2) Ring A is a benzene ring which may optionally be substituted by a halogen atom, a lower alkyl group, a halo-lower alkyl group, a lower alkoxy group, a phenyl group, or a lower alkenylene group, and Ring B is (a) an unsaturated monocyclic heterocyclic ring which may optionally be substituted by a halogen atom; a cyano group; a lower alkyl group; a halo-lower alkyl group; a phenyl-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, a mono- or di-lower alkylamino group, or a carbamoyl group; or a heterocyclyl group optionally substituted by a halogen atom, a cyano group, a lower alkyl group, a halo-lower alkyl group, a lower alkoxy group, a mono- or di-lower alkylamino group or a carbamoyl group; (b) an unsaturated fused heterobicyclic ring which may optionally be substituted by a group selected from a halogen atom, cyano group, a lower alkyl group, a halo-lower alkyl group, a phenyl-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; or (3) Ring A is an unsaturated fused heterobicyclic ring which may optionally be substituted by a halogen atom, a lower alkyl group, a halo-lower alkyl group, a lower alkoxy group, or an oxo group, and Ring B is (a) a benzene ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; (b) an unsaturated monocyclic heterocyclic ring which may optionally be substituted by a halogen atom; a cyano group; a lower alkyl group; a halo-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, or a mono- or di-lower alkylamino group; or a heterocyclyl group optionally substituted by a halogen atom, a cyano group, a lower alkyl group, a halo-lower alkyl group, a lower alkoxy group, or a mono- or di-lower alkylamino group; or (c) an unsaturated fused heterobicyclic ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group.

In another more preferable embodiment, Y is —CH$_2$— and is linked at the 3-position of Ring A, with respect to X being the 1-position, Ring A is a benzene ring which is substituted by 1-3 substituents selected from the group consisting of a lower alkyl group, a halo-lower alkyl group, a halogen atom, a lower alkoxy group, a phenyl group, and a lower alkenylene group, and Ring B is an unsaturated monocyclic heterocyclic ring or an unsaturated fused heterobicyclic ring, each of which may be substituted by 1-3 substituents selected from the group consisting of a lower alkyl group, a halo-lower alkyl group, a phenyl-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a halo-lower alkoxy phenyl group, a lower alkylenedioxyphenyl group, a lower alkyleneoxy phenyl group, a mono- or di-lower alkylaminophenyl group, a carbamoyl phenyl group, a mono- or di-lower alkylcarbamoylphenyl group, a heterocyclyl group, a haloheterocyclyl group, a cyanoheterocyclyl group, a lower alkylheterocyclyl group, a lower alkoxyheterocyclyl group, a mono- or di-lower alkylaminoheterocycyclyl group, a carbamoylheterocyclyl group, and a mono- or di-lower alkylcarbamoyl group.

In another more preferable embodiment, Y is —CH$_2$— and is linked at the 3-position of Ring A, with respect to X being the 1-position, Ring A is an unsaturated monocyclic heterocyclic ring which may be substituted by 1-3 substituents selected from the group consisting of a lower alkyl group, a halogen atom, a lower alkoxy group, and an oxo group, and Ring B is a benzene ring which may be substituted by 1-3 substituents selected from the group consisting of a lower alkyl group, a halo-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a heterocyclyl group, a haloheterocyclyl group, a cyanoheterocyclyl group, a lower alkylheterocyclyl group, and a lower alkoxyheterocyclyl group.

Further, in another preferable embodiment, Y is —CH$_2$— and is linked at the 3-position of Ring A, with respect to X being the 1-position, Ring A is an unsaturated monocyclic heterocyclic ring which may be substituted by 1-3 substituents selected from the group consisting of a lower alkyl group, a halogen atom, a lower alkoxy group, and an oxo group, and Ring B is an unsaturated monocyclic heterocyclic ring or an unsaturated fused heterobicyclic ring, each of which may be substituted by 1-3 substituents selected from the group consisting of a lower alkyl group, a halo-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a halo-lower alkoxyphenyl group, a heterocyclyl group, a haloheterocyclyl group, a cyanoheterocyclyl group, a lower alkylheterocyclyl group, and a lower alkoxyheterocyclyl group.

In a more preferable embodiment of the present invention, X is a carbon atom and Y is —CH$_2$—.

Further, in another preferable embodiment, Ring A and Ring B are (1) Ring A is a benzene ring which may optionally be substituted by 1-3 substituents, independently selected from the group consisting of a halogen atom, a lower alkyl group optionally substituted by a halogen atom or a lower alkoxy group, a lower alkoxy group optionally substituted by a halogen atom or a lower alkoxy group, a cycloalkyl group, a cycloalkoxy group, a phenyl group, and a lower alkenylene group, and Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group, a halo-lower alkoxy group, or a carbamoyl group; a heterocyclyl group optionally substituted by a halogen atom, a cyano group, a lower alkyl group, a halo-lower alkyl group, a lower alkoxy group, a halo-lower alkoxy group or a carbamoyl roup; and an oxo group;

(2) Ring A is an unsaturated monocyclic heterocyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, and Ring B is a benzene ring which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; a lower alkylene group;

(3) Ring A is an unsaturated monocyclic heterocyclic ring which may optionally be substituted by 1-3 substituents, independently selected from the group consisting of a halogen atom, a lower alkyl group optionally substituted by a halogen atom or a lower alkoxy group, a lower alkoxy group optionally substituted by a halogen atom or a lower alkoxy group, a cycloalkyl group, a cycloalkoxy group, and an oxo group, Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and an oxo group;

(4) Ring A is an unsaturated fused heterobicyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, Ring B is a benzene ring which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and a lower alkylene group, or (5) Ring A is an unsaturated monocyclic heterocyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and an oxo group.

In another preferable embodiment of the present invention, Y is linked at the 3-position of Ring A, with respect to X being the 1-position, Ring A is a benzene ring which may optionally be substituted by a halogen atom, a lower alkyl group optionally substituted by a halogen atom, a lower alkoxy group, or a phenyl group, and Ring B is an unsaturated monocyclic heterocyclic ring or an unsaturated fused heterobicyclic ring which may optionally be substituted by 1-3 substituents, independently selected from the group consisting of a halogen atom; a lower alkyl group optionally substituted by a halogen atom or a phenyl group; a lower alkoxy group; a phenyl group optionally substituted by a halogen atom, a cyano group, a lower alkyl group, a halo-lower alkyl group, or a lower alkoxy group; a heterocyclyl group optionally substituted by a halogen atom, a cyano group, a lower alkyl group, a halo-lower alkyl group, or a lower alkoxy group; and an oxo group.

In another more preferable embodiment of the present invention, Y is linked at the 3-position of Ring A, with respect to X being the 1-position, Ring A is an unsaturated monocyclic heterocyclic ring which may optionally be substituted by a substituent selected from a halogen atom, a lower alkyl group, and an oxo group, and Ring B is a benzene ring which may optionally be substituted by a substituent selected from the group consisting of a halogen atom; a lower alkyl group optionally substituted by a halogen atom or a phenyl group; a lower alkoxy group; a phenyl group optionally substituted by a halogen atom, a cyano group, a lower alkyl group, a halo-lower alkyl group, or a lower alkoxy group; a heterocyclyl group optionally substituted by a halogen atom, a cyano group, a lower alkyl group, a halo-lower alkyl group, or a lower alkoxy group; and a lower alkylene group.

Preferable examples of unsaturated monocyclic heterocyclic ring include a 5- or 6-membered unsaturated heterocyclic ring containing 1 or 2 hetero atoms independently selected from a nitrogen atom, an oxygen atom, and a sulfur atom. More specifically, preferred are furan, thiophene, oxazole, isoxazole, triazole, tetrazole, pyrazole, pyridine, pyrimidine, pyrazine, dihydroisoxazole, dihydropyridine, and thiazole. Preferable unsaturated fused heterobicyclic ring includes a 9- or 10-membered unsaturated fused heterocyclic ring containing 1 to 4 hetero atoms independently selected from a nitrogen atom, an oxygen atom, and a sulfur atom. More specifically, preferred are indoline, isoindoline, benzothiazole, benzoxazole, indole, indazole, quinoline, isoquinoline, benzothiophene, benzofuran, thienothiophene, and dihydroisoquinoline.

In a more preferred embodiment of the present invention, Ring A is a benzene ring which may optionally be substituted by a substituent selected from the group consisting of a halogen atom, a lower alkyl group, a halo-lower alkyl group, a lower alkoxy group, and a phenyl group, and Ring B is a heterocyclic ring selected from the group consisting of thiophene, furan, benzofuran, benzothiophene, and benzothiazole, wherein the heterocyclic ring may optionally be substituted by a substituent selected from the following group: a halogen atom, a cyano group, a lower alkyl group, a halo-lower alkyl group, a phenyl-lower alkyl group, a lower alkoxy group, a halo-lower alkoxy group, a phenyl group, a halophenyl group, a lower alkylphenyl group, a lower alkoxyphenyl group, a thienyl group, a halothienyl group, a pyridyl group, a halopyridyl group, and a thiazolyl group.

In yet another preferred embodiment, Y is —CH$_2$—, Ring A is an unsaturated monocyclic heterocyclic ring or an unsaturated fused heterobicyclic ring selected from the group consisting of thiophene, dihydroisoquinoline, dihydroisoxazole, triazole, pyrazole, dihydropyridine, dihydroindole, indole, indazole, pyridine, pyrimidine, pyrazine, quinoline, and a isoindoline, wherein the heterocyclic ring may optionally substituted by a substituent selected from the following group: a halogen atom, a lower alkyl group, and an oxo group, and Ring B is a benzene ring which may optionally be substituted by a substituent selected from the following group: a halogen atom, a lower alkyl group, a halo-lower alkyl group, a lower alkoxy group, and a halo-lower alkoxy group.

In a further preferred embodiment of the present invention, Ring A is a benzene ring which is substituted by a halogen atom or a lower alkyl group, and Ring B is thienyl group which is substituted by phenyl group or a heterocyclyl group in which said phenyl group and heterocyclyl group is substituted by 1-3 substituents selected from a halogen atom, a cyano group, a lower alkyl group, a halo-lower alkyl group, a lower alkoxy group, and a halo-lower alkoxy group.

Further, in another aspect of the present invention, preferable examples of the compound of the formula I include a compound wherein Ring A is

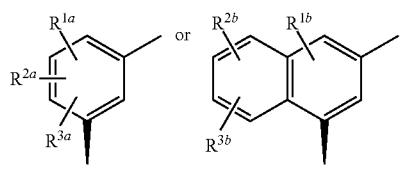

wherein $R^{1a}$, $R^{2a}$, $R^{3a}$, $R^{1b}$, $R^{2b}$, and $R^{3b}$ are each independently a hydrogen atom, a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, a phenyl group, a phenylalkoxy group, a cyano group, an amino group, a mono- or di-alkylamino group, an alkanoylamino group, a carboxyl group, an alkoxycarbonyl group, a carbamoyl group, a mono- or di-alkylcarbamoyl group, an alkanoyl group, an alkylsulfonylamino group, a phenylsulfonylamino group, an alkylsulfinyl group, an alkylsulfonyl group, or a phenylsulfonyl group, and Ring B is

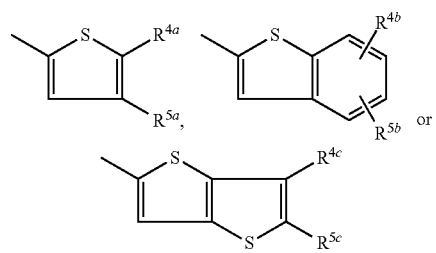

wherein $R^{4a}$ and $R^{5a}$ are each independently a hydrogen atom; a halogen atom; a hydroxy group; an alkoxy group; an alkyl group; a haloalkyl group; a haloalkoxy group; a hydroxyalkyl group; an alkoxyalkyl group; a phenylalkyl group; an alkoxyalkoxy group; a hydroxyalkoxy group; an alkenyl group; an alkynyl group; a cycloalkyl group; a cycloalkylidenemethyl group; a cycloalkenyl group; a cycloalkyloxy group; a phenyloxy group; a phenylalkoxy group; a cyano group; an amino group; a mono- or di-alkylamino group; an alkanoylamino group; a carboxyl group; an alkoxycarbonyl group; a carbamoyl group; a mono- or di-alkylcarbamoyl group; an alkanoyl group; an alkylsulfonylamino group; a phenylsulfonylamino group; an alkylsulfinyl group; an alkylsulfonyl group; a phenylsulfonyl group; a phenyl group optionally substituted by a halogen atom, a cyano group, an alkyl group, a haloalkyl group, an alkoxy group, a haloalkoxy group, an alkylenedioxy group, an alkyleneoxy group, a mono- or di-alkylamino group, a carbamoyl group, or a mono- or di-alkylcarbamoyl group; or a heterocyclyl group optionally substituted by a halogen atom, a cyano group, an alkyl group, a haloalkyl group, an alkoxy group, a haloalkoxy group, a carbamoyl group, or a mono- or di-alkylcarbamoyl group, or $R^{4a}$ and $R^{5a}$ are bonded to each other at the terminals thereof to form an alkylene group; and $R^{4b}$, $R^{5b}$, $R^{4c}$ and $R^{5c}$ are each independently a hydrogen atom; a halogen atom; a hydroxy group; an alkoxy group; an alkyl group; a haloalkyl group; a haloalkoxy group; a hydroxyalkyl group; an alkoxyalkyl group; a phenylalkyl group; an alkoxyalkoxy group; a hydroxyalkoxy group; an alkenyl group; an alkynyl group; a cycloalkyl group; a cycloalkylidenemethyl group; a cycloalkenyl group; a cycloalkyloxy group; a phenyloxy group; a phenylalkoxy group; a cyano group; an amino group; a mono- or di-alkylamino group; an alkanoylamino group; a carboxyl group; an alkoxycarbonyl group; a carbamoyl group; a mono- or di-alkylcarbamoyl group; an alkanoyl group; an alkylsulfonylamino group; a phenylsulfonylamino group; an alkylsulfinyl group; an alkylsulfonyl group; a phenylsulfonyl group; a phenyl group optionally substituted by a halogen atom, a cyano group, an alkyl group, a haloalkyl group, an alkoxy group, a haloalkoxy group, a methylenedioxy group, an ethyleneoxy group, or a mono- or di-alkylamino group; or a heterocyclyl group optionally substituted by a halogen atom, a cyano group, an alkyl group, a haloalkyl group, an alkoxy group or a haloalkoxy group.

More preferred is a compound wherein $R^{1a}$, $R^{2a}$, $R^{3a}$, $R^{1b}$, $R^{2b}$, and $R^3$ are each independently a hydrogen atom, a halogen atom, a lower alkyl group, a halo-lower alkyl group, a lower alkoxy group, or a phenyl group;

$R^{4a}$ and $R^5$ are each independently a hydrogen atom; a halogen atom; a lower alkyl group; a halo-lower alkyl group; a phenyl-lower alkyl group; a phenyl group optionally substituted by a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, or a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, or $R^{4a}$ and $R^{5a}$ are bonded to each other at the terminals thereof to form a lower alkylene group; and $R^{4b}$, $R^{5b}$, $R^{4c}$ and $R^{5c}$ are each independently a hydrogen atom, a halogen atom, a lower alkyl group, a halo-lower alkyl group, a lower alkoxy group, or a halo-lower alkoxy group.

Further preferred is a compound in which Ring B is

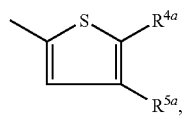

wherein $R^{4a}$ is a phenyl group optionally substituted by a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, or a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, and $R^{5a}$ is a hydrogen atom, or $R^{4a}$ and $R^{5a}$ are bonded to each other at the terminals thereof to form a lower alkylene group.

Further more preferred is a compound in which Ring A is

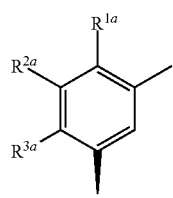

wherein $R^{1a}$ is a halogen atom, a lower alkyl group, or a lower alkoxy group, and $R^{2a}$ and $R^{3a}$ are hydrogen atoms; and Ring B is

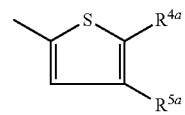

wherein $R^{4a}$ is a phenyl group optionally substituted by a substituent selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, and $R^{5a}$ is a hydrogen atom, and Y is —CH$_2$—.

In more preferable embodiment, $R^{4a}$ is a phenyl group optionally substituted by a halogen atom, a cyano group, a lower alkyl group, a halo-lower alkyl group, a lower alkoxy group, or a halo-lower alkoxy group; or a heterocyclyl group optionally substituted by a halogen atom, a cyano group, a lower alkyl group, or a lower alkoxy group.

In another preferable embodiment of the present invention, a preferable compound can be represented by the following formula IA:

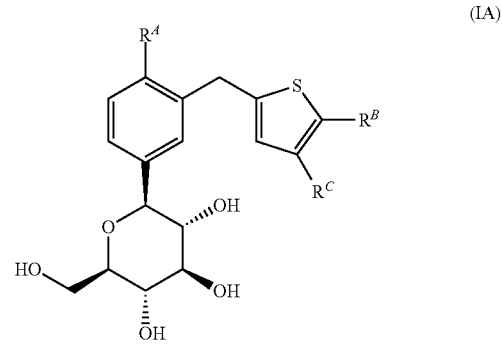

(IA)

wherein $R^A$ is a halogen atom, a lower alkyl group or a lower alkoxy group; $R^B$ is a phenyl group optionally substituted by 1-3 substituents selected from a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocycyl group optionally substituted by 1-3 substituents selected from a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group; and $R^C$ is hydrogen atom; or $R^B$ and $R^C$ taken together are a fused benzene ring which may be substituted by a halogen atom, a lower alkyl group, a halo-lower alkyl group, a lower alkoxy group or a halo-lower alkoxy group.

In a preferable embodiment, $R^A$ is a halogen atom or a lower alkyl group, $R^C$ is hydrogen atom, and $R^B$ is phenyl group substituted by 1-3 substituents selected from a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group. The chemical structure of such compounds are represented by the following formula (IA'):

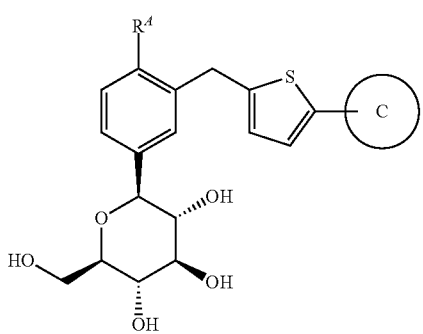

wherein $R^A$ is a halogen atom, or a lower alkyl group, Ring C is a phenyl group substituted by 1-3 substituents selected from the group consisting of a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group.

In a more preferable embodiment, Ring C is a phenyl group substituted by 1-3 substituents selected from the group consisting of a halogen atom, a cyano group, a lower alkyl group, a halo-lower alkyl group, a lower alkoxy group, a halo-lower alkoxy group, and a mono- or di-lower alkylamino group; or a heterocyclyl group substituted by a substituent selected from the group consisting of a halogen atom, a cyano group, a lower alkyl group, a halo-lower alkyl group, a lower alkoxy group, and a halo-lower alkoxy group.

Among them, a compound in which Ring C is a phenyl group substituted by a halogen atom, a cyano group, a lower alkyl group, a halo-lower alkyl group, a lower alkoxy group or a halo-lower alkoxy group; or a heterocyclyl group substituted by a halogen atom, a cyano group, a lower alkyl group, or a lower alkoxy group is preferred.

A preferred heterocyclyl group includes a 5- or 6-membered heterocyclyl group containing 1 or 2 hetero atoms independently selected from the group consisting of a nitrogen atom, an oxygen atom, and a sulfur atom, or a 9- or 10-membered heterocyclyl group containing 1 to 4 hetero atoms independently selected from the group consisting of a nitrogen atom, an oxygen atom, and a sulfur atom. Specifically, a thienyl group, a pyridyl group, a pyrimidyl group, a pyrazinyl group, pyrazolyl group, a thiazolyl group, a quinolyl group, a tetrazolyl group and an oxazolyl group are preferred.

In a further preferable embodiment, Ring C is a phenyl group substituted by a halogen atom or a cyano group, or a pyridyl group substituted by a halogen atom.

In another preferable embodiment of the present invention, preferred is a compound in which Ring A is

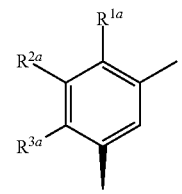

wherein $R^{1a}$ is a halogen atom, a lower alkyl group, or a lower alkoxy group, and $R^{2a}$ and $R^{3a}$ are hydrogen atoms; and Ring B is

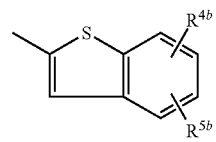

wherein $R^{4b}$ and $R^{5b}$ are each independently a hydrogen atom, a halogen atom, a lower alkyl group, a halo-lower alkyl group, a lower alkoxy group, or a halo-lower alkoxy group.

Preferred compound of the present invention may be selected from the following group: 1-(β-D-glucopyranosyl)-4-chloro-3-[5-(5-thiazolyl)-2-thienylmethyl]benzene; 1-(β-D-glucopyranosyl)-4-chloro-3-(5-phenyl-2-thienylmethyl)benzene; 1-(β-D-glucopyranosyl)-4-methyl-3-[5-(4-fluorophenyl)-2-thienylmethyl]benzene; 1-(β-D-glucopyranosyl)-4-chloro-3-[5-(2-pyrimidinyl)-2-thienylmethyl]benzene; 1-(βD-glucopyranosyl)-4-methyl-3-[5-(2-pyrimidinyl)-2-thienylmethyl]benzene; 1-(β-D-glucopyranosyl)-4-chloro-3-[5-(3-cyanophenyl)-2-thienylmethyl]benzene; 1-(β-D-glucopyranosyl)-4-chloro-3-[5-(4-cyanophenyl)-2-thienylmethyl]benzene; 1-(β-D-glucopyranosyl)-4-methyl-3-[5-(6-fluoro-2-pyridyl)-2-thienylmethyl]benzene; 1-(β-D-glucopyranosyl)-4-chloro-3-[5-(6-fluoro-2-pyridyl)-2-thienylmethyl]benzene; 1-(β-D-glucopyranosyl)-4-methyl-3-[5-(3-difluoromethyl-phenyl)-2-thienylmethyl]benzene; 1-(β-D-glucopyranosyl)-4-methyl-3-[5-(3-cyanophenyl)-2-thienylmethyl]benzene; 1-(β-D-glucopyranosyl)-4-methyl-3-[5-(4-cyanophenyl)-2-thienylmethyl]benzene; 1-(β-D-glucopyranosyl)-4-chloro-3-[5-(6-fluoro-3-pyridyl)-2-thienylmethyl]benzene; 1-(β-D-glucopyranosyl)-4-fluoro-3-(5-(3-cyanophenyl)-2-thienylmethyl)benzene; the pharmaceutically acceptable salt thereof; and the prodrug thereof.

Particularly preferred compounds of the present invention include: 1-(β-D-glucopyranosyl)-4-methyl-3-[5-(3-cyanophenyl)-2-thienylmethyl]benzene, or a pharmaceutically acceptable salt thereof, or a prodrug thereof; 1-(β-D-glucopyranosyl)-4-methyl-3-[5-(4-cyano-phenyl)-2-thienylmethyl]benzene, or a pharmaceutically acceptable salt thereof, or a prodrug thereof; 1-(β-D-glucopyranosyl)-4-methyl-3-[5-(4-fluoro-phenyl)-2-thienylmethyl]benzene, or a pharmaceutically acceptable salt thereof, or a prodrug thereof;

1-(β-D-glucopyranosyl)-4-chloro-3-[5-(3-cyano-phenyl)-2-thienylmethyl]benzene, or a pharmaceutically acceptable salt thereof, or a prodrug thereof; 1-(β-D-glucopyranosyl)-4-methyl-3-[5-(6-fluoro-2-pyridyl)-2-thienylmethyl]benzene, or a pharmaceutically acceptable salt thereof, or a prodrug thereof; 1-(β-D-glucopyranosyl)-4-chloro-3-[5-(6-fluoro-2-pyridyl)-2-thienylmethyl]benzene, or a pharmaceutically acceptable salt thereof, or a prodrug thereof; 1-(β-D-glucopyranosyl)-4-chloro-3-[5-(6-fluoro-3-pyridyl)-2-thienylmethyl]benzene, or a pharmaceutically acceptable salt thereof, or a prodrug thereof; and 1-(β-D-glucopyranosyl)-4-fluoro-3-(5-(3-cyanophenyl)-2-thienylmethyl)benzene, or a pharmaceutically acceptable salt thereof, or a prodrug thereof.

In an embodiment, the compound of formula (I) is selected from the group consisting of compounds of formula (I-Q):

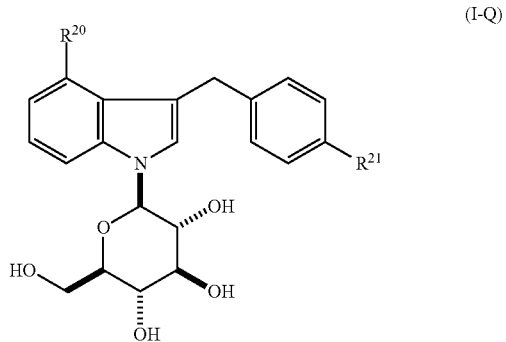

(I-Q)

wherein
R$^{20}$ is selected from the group consisting of hydrogen and fluorine;
R$^{21}$ is selected from the group consisting of ethyl and cyclopropyl;
and pharmaceutically acceptable salts thereof.

In an embodiment of the present invention, the compound of formula (I) is a compound of formula (I-Q) wherein R$^{20}$ is hydrogen. In another embodiment of the present invention, the compound of formula (I) is a compound of formula (I-Q) wherein R$^{20}$ is fluorine. In another embodiment of the present invention, the compound of formula (I) is a compound of formula (I-Q) wherein R$^{21}$ is ethyl. In another embodiment of the present invention, the compound of formula (I) is a compound of formula (I-Q) wherein R$^{21}$ is cyclopropyl. In another embodiment of the present invention, the compound of formula (I) is a compound of formula (I-Q) wherein R$^{20}$ is fluorine and R$^{21}$ is cyclopropyl. In another embodiment of the present invention, the compound of formula (I) is a compound of formula (I-Q) wherein R$^{20}$ is hydrogen and R$^{21}$ is ethyl.

The term "halogen atom" or "halo" means chlorine, bromine and fluorine; wherein chlorine and fluorine are preferable.

The term "alkyl group" means a straight or branched saturated monovalent hydrocarbon chain having 1 to 12 carbon atoms. The straight chain or branched chain alkyl group having 1 to 6 carbon atoms is preferable, and the straight chain or branched chain alkyl group having 1 to 4 carbon atoms is more preferable. Examples thereof are methyl group, ethyl group, propyl group, isopropyl group, butyl group, t-butyl group, isobutyl group, pentyl group, hexyl group, isohexyl group, heptyl group, 4,4-dimethylpentyl group, octyl group, 2,2,4-trimethylpentyl group, nonyl group, decyl group, and various branched chain isomers thereof. Further, the alkyl group may optionally and independently be substituted by 1 to 4 substituents as listed below, if necessary.

The term "alkylene group" or "alkylene" means a straight or branched divalent saturated hydrocarbon chain having 1 to 12 carbon atoms. The straight chain or branched chain alkylene group having 1 to 6 carbon atoms is preferable, and the straight chain or branched chain alkylene group having 1 to 4 carbon atoms is more preferable. Examples thereof are methylene group, ethylene group, propylene group, trimethylene group, etc. If necessary, the alkylene group may optionally be substituted in the same manner as the above-mentioned "alkyl group". Where alkylene groups as defined above attach at two different carbon atoms of the benzene ring, they form an annelated five, six or seven membered carbocycle together with the carbon atoms to which they are attached, and may optionally be substituted by one or more substituents defined below.

The term "alkenyl group" means a straight or branched monovalent hydrocarbon chain having 2 to 12 carbon atoms and having at least one double bond. Preferable alkenyl group is a straight chain or branched chain alkenyl group having 2 to 6 carbon atoms, and the straight chain or branched chain alkenyl group having 2 to 4 carbon atoms is more preferable. Examples thereof are vinyl group, 2-propenyl group, 3-butenyl group, 2-butenyl group, 4-pentenyl group, 3-pentenyl group, 2-hexenyl group, 3-hexenyl group, 2-heptenyl group, 3-heptenyl group, 4-heptenyl group, 3-octenyl group, 3-nonenyl group, 4-decenyl group, 3-undecenyl group, 4-dodecenyl group, 4,8,12-tetradecatrienyl group, etc. The alkenyl group may optionally and independently be substituted by 1 to 4 substituents as mentioned below, if necessary.

The term "alkenylene group" means a straight or branched divalent hydrocarbon chain having 2 to 12 carbon atoms and having at least one double bond. The straight chain or branched chain alkenylene group having 2 to 6 carbon atoms is preferable, and the straight chain or branched chain alkenylene group having 2 to 4 carbon atoms is more preferable. Examples thereof are vinylene group, propenylene group, butadienylene group, etc. If necessary, the alkylene group may optionally be substituted by 1 to 4 substituents as mentioned below, if necessary. Where alkenylene groups as defined above attach at two different carbon atoms of the benzene ring, they form an annelated five, six or seven membered carbocycle (e.g., a fused benzene ring) together with the carbon atoms to which they are attached, and may optionally be substituted by one or more substituents defined below.

The term "alkynyl group" means a straight or branched monovalent hydrocarbon chain having at least one triple bond. The preferable alkynyl group is a straight chain or branched chain alkynyl group having 2 to 6 carbon atoms, and the straight chain or branched chain alkynyl group having 2 to 4 carbon atoms is more preferable. Examples thereof are 2-propynyl group, 3-butynyl group, 2-butynyl group, 4-pentynyl group, 3-pentynyl group, 2-hexynyl group, 3-hexynyl group, 2-heptynyl group, 3-heptynyl group, 4-heptynyl group, 3-octynyl group, 3-nonynyl group, 4-decynyl group, 3-undecynyl group, 4-dodecynyl group, etc. The alkynyl group may optionally and independently be substituted by 1 to 4 substituents as mentioned below, if necessary.

The term "cycloalkyl group" means a monocyclic or bicyclic monovalent saturated hydrocarbon ring having 3 to 12 carbon atoms, and the monocyclic saturated hydrocarbon group having 3 to 7 carbon atoms is more preferable. Examples thereof are a monocyclic alkyl group and a bicyclic alkyl group such as cyclopropyl group, cyclobutyl group, cyclopentyl group, cyclohexyl group, cycloheptyl group, cyclooctyl group, cyclodecyl group, etc. These groups may optionally and independently be substituted by 1 to 4 substituents as mentioned below, if necessary. The cycloalkyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the condensed unsaturated hydrocarbon ring may be optionally and independently be substituted by 1 to 4 substituents as mentioned below.

The term "cycloalkylidene group" means a monocyclic or bicyclic divalent saturated hydrocarbon ring having 3 to 12 carbon atoms, and the monocyclic saturated hydrocarbon group having 3 to 6 carbon atoms is preferable. Examples thereof are a monocyclic alkylidene group and a bicyclic alkylidene group such as cyclopropylidene group, cyclobutylidene group, cyclopentylidine group, cyclohexylidene group, etc. These groups may optionally and independently be substituted by 1 to 4 substituents as mentioned below, if necessary. Besides, the cycloalkylidene group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the unsaturated hydrocarbon ring may be optionally and independently be substituted by 1 to 4 substituents as mentioned below.

The term "cycloalkenyl group" means a monocyclic or bicyclic monovalent unsaturated hydrocarbon ring having 4 to 12 carbon atoms and having at least one double bond. The preferable cycloalkenyl group is a monocyclic unsaturated hydrocarbon group having 4 to 7 carbon atoms. Examples thereof are monocyclic alkenyl groups such as cyclopentenyl group, cyclopentadienyl group, cyclohexenyl group, etc. These groups may optionally and independently be substituted by 1 to 4 substituents as mentioned below, if necessary. Besides, the cycloalkenyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the unsaturated hydrocarbon ring may be optionally and independently be substituted by 1 to 4 substituents as mentioned below.

The term "cycloalkynyl group" means a monocyclic or bicyclic unsaturated hydrocarbon ring having 8 to 12 carbon atoms, and having at least one triple bond. The preferable cycloalkynyl group is a monocyclic unsaturated hydrocarbon group having 8 to 10 carbon atoms. Examples thereof are monocyclic alkynyl groups such as cyclooctynyl group, cyclodecynyl group. These groups may optionally be substituted by 1 to 4 substituents as mentioned below, if necessary. Besides, the cycloalkynyl group may optionally and independently be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring or the unsaturated hydrocarbon ring may be optionally and independently be substituted by 1 to 4 substituents as mentioned below.

The term "aryl group" means a monocyclic or bicyclic monovalent aromatic hydrocarbon group having 6 to 10 carbon atoms. Examples thereof are phenyl group, naphthyl group (including 1-naphthyl group and 2-naphthyl group). These groups may optionally and independently be substituted by 1 to 4 substituents as mentioned below, if necessary. Besides, the aryl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring or the unsaturated hydrocarbon ring may be optionally and independently be substituted by 1 to 4 substituents as mentioned below.

The term "unsaturated monocyclic heterocyclic ring" means an unsaturated hydrocarbon ring containing 1-4 heteroatoms independently selected from a nitrogen atom, an oxygen atom and a sulfur atom, and the preferable one is a 4- to 7-membered unsaturated hydrocarbon ring containing 1-4 heteroatoms independently selected from a nitrogen atom, an oxygen atom and a sulfur atom. Examples thereof are pyridine, pyrimidine, pyrazine, furan, thiophene, pyrrole, imidazole, pyrazole, oxazole, isoxazole, 4,5-dihydrooxazole, thiazole, isothiazole, thiadiazole, triazole, tetrazole, etc. Among them, pyridine, pyrimidine, pyrazine, furan, thiophene, pyrrole, imidazole, oxazole, and thiazole can be preferably used. The "unsaturated monocyclic heterocyclic ring" may optionally and independently be substituted by 1-4 substituents as mentioned below, if necessary.

The term "unsaturated fused heterobicyclic ring" means hydrocarbon ring comprised of a saturated or a unsaturated hydrocarbon ring condensed with the above mentioned unsaturated monocyclic heterocyclic ring where said saturated hydrocarbon ring and said unsaturated hydrocarbon ring may optionally contain an oxygen atom, a nitrogen atom, a sulfur atom, SO, or $SO_2$ within the ring, if necessary. The "unsaturated fused heterobicyclic ring" includes, for example, benzothiophene, indole, tetrahydrobenzothiophene, benzofuran, isoquinoline, thienothiophene, thienopyridine, quinoline, indoline, isoindoline, benzothiazole, benzoxazole, indazole, dihydroisoquinoline, etc. Further, the "heterocyclic ring" also includes possible N- or S-oxides thereof.

The term "heterocyclyl" means a monovalent group of the above-mentioned unsaturated monocyclic heterocyclic ring or unsaturated fused heterobicyclic ring and a monovalent group of the saturated version of the above-mentioned unsaturated monocyclic heterocyclic or unsaturated fused heterobicyclic ring. If necessary, the heterocyclyl may optionally and independently be substituted by 1 to 4 substituents as mentioned below.

The term "alkanoyl group" means a formyl group and ones formed by binding an "alkyl group" to a carbonyl group.

The term "alkoxy group" means ones formed by binding an "alkyl group" to an oxygen atom.

The substituent for the above each group includes, for example, a halogen atom (fluorine, chlorine, bromine), a cyano group, an oxo group, a hydroxy group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a hetero-cyclylcarbonyl group, an alkoxy-carbonyl group, an alkenyloxy-carbonyl group, an alkynyloxy-carbonyl group, a cycloalkyloxy-carbonyl group, a cycloalkenyloxy-carbonyl group, a cycloalkynyloxycarbonyl group, an aryloxycarbonyl group, a heterocyclyloxycarbonyl group, an alkanoyloxy group, an alkenyl-carbonyloxy group, an alkynyl-carbonyloxy group, a cycloalkyl-carbonyloxy group, a cycloalkenylcarbonyloxy group, a cycloalkynyl-carbonyloxy group, an arylcarbonyloxy group, a heterocyclylcarbonyloxy group, an alkylthio group, an alkenyl-thio group, an alkynylthio group, a cycloalkylthio group, a cycloalkenyl-thio group, a cycloalkynylthio group, an arylthio group, a heterocyclylthio group, an amino group, a mono- or di-alkyl-amino group, a mono- or di-alkanoylamino group, a mono- or di-alkoxy-carbonyl-amino group, a mono- or di-arylcarbonyl-amino group, an alkylsulfinylamino group, an alkyl-sulfonyl-amino group, an arylsulfinylamino group, an arylsulfonylamino group, a carbamoyl group, a mono- or di-alkyl-carbamoyl group, a mono- or di-arylcarbamoyl group, an alkylsulfinyl group, an alkenylsulfinyl group, an alkynylsulfinyl group, a cycloalkyl-sulfinyl group, a cycloalkenylsulfinyl group, a cycloalkynyl-sulfinyl group, an arylsulfinyl group, a heterocyclyl-sulfinyl group, an alkyl-sulfonyl group, an alkenylsulfonyl group, an alkynylsulfonyl group, a cycloalkylsulfonyl group, a cycloalkenyl-sulfonyl group, a cycloalkynylsulfonyl group, an arylsulfonyl group, and a heterocyclylsulfonyl group. Each group as mentioned above may optionally be substituted by these substituents.

Further, the terms such as a haloalkyl group, a halo-lower alkyl group, a haloalkoxy group, a halo-lower alkoxy group, a halophenyl group, or a haloheterocyclyl group mean an alkyl group, a lower alkyl group, an alkoxy group, a lower alkoxy group, a phenyl group or a heterocyclyl group (hereinafter, referred to as an alkyl group, etc.) being substituted by one or more halogen atoms, respectively. Preferable ones are an alkyl group, etc. being substituted by 1 to 7 halogen atoms, and more preferable ones are an alkyl group, etc. being substituted by 1 to 5 halogen atoms. Similarly, the terms such as a hydroxyalkyl group, a hydroxy-lower alkyl group, a hydroxyalkoxy group, a hydroxy-lower alkoxy group and a hydroxyphenyl group mean an alkyl group, etc., being substituted by one or more hydroxy groups. Preferable ones are an alkyl group, etc., being substituted by 1 to 4 hydroxy groups, and more preferable ones are an alkyl group, etc., being substituted by 1 to 2 hydroxy groups. Further, the terms such as an alkoxyalkyl group, a lower alkoxyalkyl group, an alkoxy-lower alkyl group, a lower alkoxy-lower alkyl group, an alkoxyalkoxy group, a lower alkoxyalkoxy group, an alkoxy-lower alkoxy group, a lower alkoxy-lower alkoxy group, an alkoxyphenyl group, and a lower alkoxyphenyl group means an alkyl group, etc., being substituted by one or more alkoxy groups. Preferable ones are an alkyl group, etc., being substituted by 1 to 4 alkoxy groups, and more preferable ones are an alkyl group, etc., being substituted by 1 to 2 alkoxy groups.

The terms "arylakyl" and "arylalkoxy" as used alone or as part of another group refer to alkyl and alkoxy groups as described above having an aryl substituent.

The term "lower" used in the definitions for the formulae in the present specification means a straight or branched carbon chain having 1 to 6 carbon atoms, unless defined otherwise. More preferably, it means a straight or branched carbon chain having 1 to 4 carbon atoms.

The term "prodrug" means an ester or carbonate, which is formed by reacting one or more hydroxy groups of the compound of the formula I with an acylating agent substituted by an alkyl, an alkoxy or an aryl by a conventional method to produce acetate, pivalate, methylcarbonate, benzoate, etc. Further, the prodrug includes also an ester or amide, which is similarly formed by reacting one or more hydroxy groups of the compound of the formula I with an α-amino acid or a β-amino acid, etc. using a condensing agent by a conventional method.

The pharmaceutically acceptable salt of the compound of the formula I includes, for example, a salt with an alkali metal such as lithium, sodium, potassium, etc.; a salt with an alkaline earth metal such as calcium, magnesium, etc.; a salt with zinc or aluminum; a salt with an organic base such as ammonium, choline, diethanolamine, lysine, ethylenediamine, t-butylamine, t-octylamine, tris(hydroxymethyl)aminomethane, N-methyl glucosamine, triethanolamine and dehydroabietylamine; a salt with an inorganic acid such as hydrochloric acid, hydrobromic acid, hydroiodic acid, sulfuric acid, nitric acid, phosphoric acid, etc.; or a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, etc.; or a salt with an acidic amino acid such as aspartic acid, glutamic acid, etc.

The compound of the present invention also includes a mixture of stereoisomers, or each pure or substantially pure isomer. For example, the present compound may optionally have one or more asymmetric centers at a carbon atom containing any one of substituents. Therefore, the compound of the formula I may exist in the form of enantiomer or diastereomer, or a mixture thereof. When the present compound (I) contains a double bond, the present compound may exist in the form of geometric isomerism (cis-compound, trans-compound), and when the present compound (I) contains an unsaturated bond such as carbonyl, then the present compound may exist in the form of a tautomer, and the present compound also includes these isomers or a mixture thereof. The starting compound in the form of a racemic mixture, enantiomer or diastereomer may be used in the processes for preparing the present compound. When the present compound is obtained in the form of a diastereomer or enantiomer, they can be separated by a conventional method such as chromatography or fractional crystallization.

In addition, the present compound of formula (I) includes an intramolecular salt, hydrate, solvate or polymorphism thereof.

As used herein, unless otherwise noted, the term "isolated form" shall mean that the compound is present in a form which is separate from any solid mixture with another compound(s), solvent system or biological environment. In an embodiment, the present invention is directed to a process for the preparation of a compound of formula (I) as an isolated form. In another embodiment, the present invention is directed to a process for the preparation of a compound of formula (I-S) as an isolated form. In another embodiment, the present invention is directed to a process for the preparation of a compound of formula (I-T) as an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment, the present invention is directed to a process for the preparation of a compound of formula (I) as a substantially pure form. In another embodiment, the present invention is directed to a process for the preparation of a compound of formula (I-S) as a substantially pure form. In another embodiment, the present invention is directed to a process for the preparation of a compound of formula (I-T) as a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment, the present invention is directed to a process for the preparation of a compound of formula (I) substantially free of corresponding sat form(s). In another embodiment, the present invention is directed to a process for the preparation of a compound of formula (I-S) substantially free of corresponding sat form(s). In another embodiment, the present invention is directed to a process for the preparation of a compound of formula (I-T) substantially free of corresponding sat form(s).

The compounds of formula (I) of the present invention exhibit an excellent inhibitory activity against sodium-dependent glucose transporter, and an excellent blood glucose lowering effect. Therefore, the compound of the present invention is useful for treating or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension. In particular, the compound of the present invention is useful in the treatment or the prophylaxis of diabetes mellitus (type 1 and type 2 diabetes mellitus, etc.), diabetic complications (such as diabetic retinopathy, diabetic neuropathy, diabetic nephropathy) or obesity, or is useful in the treatment of postprandial hyperglycemia.

The compounds of formula (I) of the present invention or a pharmaceutically acceptable salt thereof may be administered either orally or parenterally, and can be used in the form of a suitable pharmaceutical preparation. Suitable pharmaceutical preparation for oral administration includes, for example, solid preparation such as tablets, granules, capsules, powders, etc., or solution preparations, suspension preparations, or emulsion preparations, etc. Suitable pharmaceutical preparation for parenteral administration includes, for example, suppositories; injection preparations and intravenous drip preparations using distilled water for injection, physiological saline solution or aqueous glucose solution; or inhalant preparations.

The dosage of the present compound of formula (I) (preferably the compound of formula (i-S) or the compound of formula (I-T)) or a pharmaceutically acceptable salt thereof may vary according to the administration routes, ages, body weight, conditions of a patient, or kinds and severity of a disease to be treated, and it is usually in the range of from about 0.01 to about 300 mg/kg/day, or any amount or range therein, preferably in the range of from about 0.1 to about 100 mg/kg/day, or any amount or range, preferably in the range of from about 0.1 to about 50 mg/kg/day, or any amount or range therein, more preferably in the range of from about 0.01 mg/kg/day to about 30 mg/kg/day, or any amount or range therein.

The compounds of the formula (I) may be used, if necessary, in combination with one or more of other antidiabetic agents, one or more agents for treating diabetic complications, and/or one or more agents for treatment of other diseases. The present compound and these other agents may be administered in the same dosage form, or in a separate oral dosage form or by injection.

The other antidiabetic agents include, for example, antidiabetic or antihyperglycemic agents including insulin, insulin secretagogues, or insulin sensitizers, or other antidiabetic agents having an action mechanism different from SGLT inhibition, and 1, 2, 3 or 4 of these other antidiabetic agents may preferably be used. Concrete examples thereof are biguanide compounds, sulfonylurea compounds, α-glucosidase inhibitors, PPARγ agonists (e.g., thiazolidinedione compounds), PPARα/γ dual agonists, dipeptidyl peptidase IV (DPP4) inhibitors, mitiglinide compounds, and/or nateglinide compounds, and insulin, glucagon-like peptide-1 (GLP-1), PTP1B inhibitors, glycogen phosphorylase inhibitors, RXR modulators, and/or glucose 6-phosphatase inhibitors.

The agents for treatment of other diseases include, for example, an anti-obesity agent, an antihypertensive agent, an antiplatelet agent, an anti-atherosclerotic agent and/or a hypolipidemic agent.

The SGLT inhibitors of the formula I may be used in combination with agents for treatment of diabetic complications, if necessary. These agents include, for example, PKC inhibitors and/or ACE inhibitors.

The dosage of those agents may vary according to ages, body weight, and conditions of patients, and administration routes, dosage forms, etc.

These pharmaceutical compositions may be orally administered to mammalian species including human beings, apes, dogs, etc., for example, in the dosage form of tablet, capsule, granule or powder, or parenterally administered in the form of injection preparation, or intranasally, or in the form of transdermal patch.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2=CH-CH_2-$, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to a oxygen atom to protect said oxygen atom from participating in a reaction and which may be readily removed following the reaction. Suitable oxygen protecting groups include, but are not limited to, acetyl, benzoyl, t-butyldimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

One skilled in the art will recognize that wherein a reaction step of the present invention may be carried out in a variety of solvents or solvent systems, said reaction step may also be carried out in a mixture of the suitable solvents or solvent systems. One skilled in the art will further recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Abbreviations used in the specification, particularly the Schemes and Examples, are as follows $BF_3.Et_2O$=Boron trifluoride diethyl etherate
DCE=Dichloroethane
DCM=Dichloromethane
DMF=N,N-Dimethylformamide
DMSO=Dimethylsulfoxide
Et=Ethyl (i.e. —$CH_2CH_3$)
EtOAc=Ethyl Acetate
EtOH=Ethanol
$Et_3SiH$=Triethylsilane
HPLC=High Pressure Liquid Chromatography
MeCN=Acetonitrile
MeOH=Methanol
2-methyl-THF=2-Methyl-tetrahydrofuran
MTBE=Methyl t-Butyl Ether
NaOAc=Sodium Acetate
NBS=N-Bromosuccinimide
pXRD=Powder X-ray Diffraction
SGLT=Sodium-dependent Glucose Transporter
THF=Tetrahydrofuran The present invention is directed to a process for the preparation of compounds of formula (I), as outlined in more detail in Scheme 1.

Scheme 1

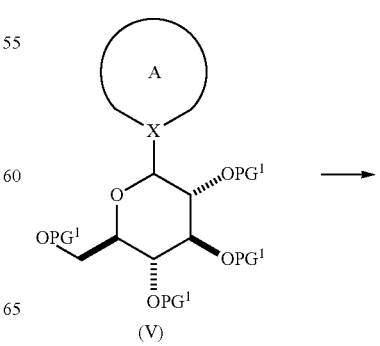

(V)

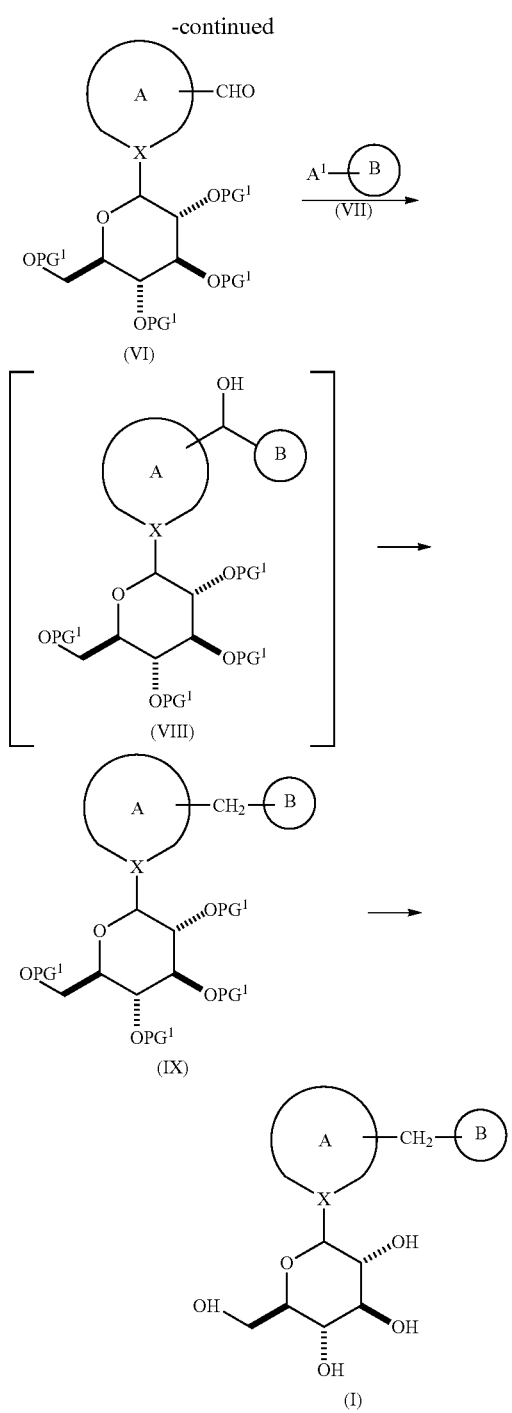

in the presence of a suitably selected carbonyl source such as DMF, and the like; wherein the carbonyl source is preferably present in an amount in the range of form about 1.0 to about 2.0 molar equivalents (relative to the moles of the compound of formula (V)), more preferably in an amount in the range of from about 1.25 to about 1.5 molar equivalents;

in a suitably selected first organic solvent such as DCE, methylene chloride, toluene, chlorobenzene, dichlorobenzene, and the like, or mixture thereof; preferably at a temperature in the range of from about room temperature to about 40° C.; to yield the corresponding compound of formula (VI).

Preferably, the reaction mixture resulting from the reaction of the compound of formula (V) with the acylating reagent is quenched to remove excess, un-reacted acetylating reagent (particularly when the acylating reagent is phosphoryl chloride), by adding the reaction mixture into a warmed, aqueous sodium acetate or warmed, aqueous potassium acetate solution. Preferably, the reaction mixture is added to a 3M aqueous sodium acetate solution warmed to about 40° C.

The compound of formula (VI) is reacted with a suitably substituted compound of formula (VII), wherein $A^1$ is a suitably selected MgBr, MgCl, and the like, a known compound or compound prepared by known methods; wherein the compound of formula (VII) is preferably present in an amount in the range of from about 1.0 to about 3.0 molar equivalents (relative to the moles of the compound of formula (VI)), more preferably in an amount in the range of from about 1.25 to about 1.75 molar equivalents;

in a suitably selected anhydrous organic solvent such as THF, 2methyl-THF, MTBE, cyclopentyl methyl ether, and the like, or mixture thereof; preferably a temperature in the range of from about −20° C. to about 0° C.; to yield the corresponding compound of formula (VIII), which compound is preferably not isolated.

Alternatively, a suitably substituted compound of formula (VII) wherein $A^1$ is a halogen such as Cl, Br, and the like, is treated with n-butyl lithium, and the like; to effect metal-halogen exchange; and the resulting mixture is reacted with the compound of formula (VI); wherein the compound of formula (VII) is preferably present in an amount in the range of from about 1.0 to about 2.0 molar equivalents (relative to the moles of the compound of formula (VI)), more preferably in an amount in the range of from about 1.0 to about 1.2 molar equivalents;

in a suitably selected anhydrous organic solvent such as THF, 2methyl-THF, MTBE, cyclopentyl methyl ether, and the like, or mixture thereof; preferably a temperature in the range of from about −50° C. to about 0° C.; to yield the corresponding compound of formula (VIII), which compound is preferably not isolated.

The compound of formula (VIII) is reacted with a suitably selected reducing agent such as $Et_3SiH$, sodium borohydride, and the like; wherein the reducing agent is preferably present in an amount in the range of from about 1.0 to about 5.0 molar equivalents (relative to the moles of the compound of formula (VIII)), more preferably in an amount in the range of from about 1.0 to about 2.0 molar equivalents;

in the presence of a suitably selected Lewis acid such as $BF_3.Et_2O$, and the like: (preferably, wherein $PG^1$ is acetyl, the Lewis acid is selected to remove the hydroxy group without removing the acetyl protecting groups); wherein the Lewis acid is preferably present in an amount in the range of from about 1.0 to about 3.0 molar equivalents (relative to the moles of the com- Accordingly, a suitably substituted compound of formula (V), wherein $PG^1$ is a suitably selected oxygen protecting group, such as acetyl, benzoyl, and the like, preferably acetyl, a known compound or compound prepared by known methods, is reacted with a suitably selected acylating reagent such as phosphoryl chloride, thionyl chloride, oxalyl chloride, and the like; wherein the acylating reagent is preferably present in an amount in the range of from about 1.5 to about 3.0 molar equivalents (relative to the moles of the compound of formula (V)), more preferably in an amount in the range of from about 2.0 to about 3.0 molar equivalents;

pound of formula (VIII)), more preferably in an amount in the range of from about 1.0 to about 1.5 molar equivalents;

in a suitably selected second organic solvent such as DCM, acetonitrile, DCE, MTBE, cyclopentyl methyl ether, and the like, or mixture thereof; preferably, at a temperature in the range of from about −20° C. to about 0° C. (during addition of reagents), followed by warming to room temperature; to yield the corresponding compound of formula (IX). Preferably, the compound of formula (IX) is purified, according to known methods, for example, by recrystallization from a suitably selected solvent such as ethanol, and the like.

The compound of formula (IX) is de-protected according to known methods, to yield the corresponding compound of formula (I). For example wherein $PG^1$ is acetyl or benzoyl, the compound of formula (IX) is reacted with a suitably selected base such as sodium methoxide, potassium carbonate, and the like, preferably sodium methoxide; in an organic solvent or mixture of organic solvents, such as methanol, THF, ethanol, isopropanol, and the like, preferably in mixture of methanol and THF; to yield the corresponding compound of formula (I). The compound of formula (I) is preferably isolated according to known methods, for example by solvent evaporation, crystallization, column chromatography, and the like.

One skilled in the art will recognize, that the compound of formula (VIII) may alternatively be reacted with a suitably selected second Lewis acid, such as $AlCl_3$, titanium tetrachloride, and the like, which second Lewis acid removes both the hydroxy group and the $PG^1$ protecting groups, simultaneously; wherein the second Lewis acid is preferably present in an amount in the range of from about 1.0 to about 10.0 molar equivalents (relative to the moles of the compound of formula (VIII)), more preferably in an amount in the range of from about 1.5 to about 6.0 molar equivalents;

in a suitably selected third organic solvent such as DCM, acetonitrile, DCE, MTBE, cyclopentyl methyl ether, and the like, or mixture thereof; optionally at a temperature greater than room temperature, preferably at a temperature in the range of from about room temperature to about 65° C.; to yield the corresponding compound of formula (I) in a single step. For example, wherein $PG^1$ is acetyl, the compound of formula (VIII) may be reacted with $AlCl_3$, to yield the corresponding compound of formula (I).

In an embodiment, the present invention is directed to a process for the preparation of a compound of formula (I-S) or a pharmaceutically acceptable salt thereof, as outlined in more detail in Scheme 2.

Scheme 2

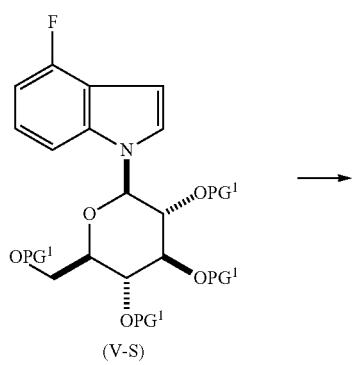

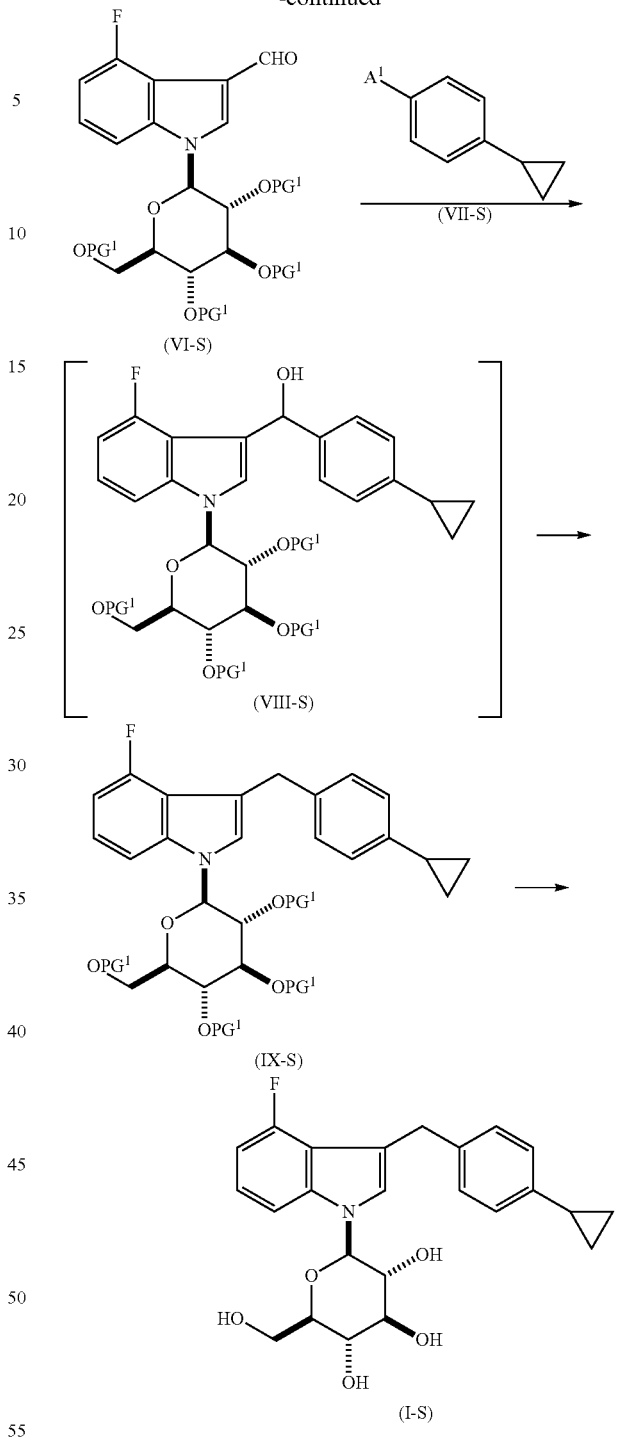

Accordingly, a suitably substituted compound of formula (V-S), wherein $PG^1$ is a suitably selected oxygen protecting group, such as acetyl, benzoyl, and the like, preferably acetyl, a known compound or compound prepared by known methods, is reacted with a suitably selected acylating reagent such as phosphoryl chloride, thionyl chloride, oxalyl chloride, and the like; wherein the acylating reagent is preferably present in an amount in the range of from about 1.5 to about 3.0 molar equivalents (relative to the moles of the compound of formula (V-S)), more preferably in an amount in the range of from about 2.0 to about 3.0 molar equivalents;

in the presence of a suitably selected carbonyl source such as DMF, and the like; wherein the carbonyl source is preferably present in an amount in the range of form about 1.0 to about 2.0 molar equivalents (relative to the moles of the compound of formula (V-S)), more preferably in an amount in the range of from about 1.25 to about 1.5 molar equivalents;

in a suitably selected first organic solvent such as DCE, methylene chloride, toluene, chlorobenzene, dichlorobenzene, and the like, or mixture thereof; preferably at a temperature in the range of from about room temperature to about 40° C.; to yield the corresponding compound of formula (VI-S).

Preferably, the reaction mixture resulting from the reaction of the compound of formula (V-S) with the acylating reagent is quenched to remove excess, un-reacted acetylating reagent (particularly when the acylating reagent is phosphoryl chloride), by adding the reaction mixture into a warmed, aqueous sodium acetate or warmed, aqueous potassium acetate solution. Preferably, the reaction mixture is added to a 3M aqueous sodium acetate solution warmed to about 40° C.

The compound of formula (VI-S) is reacted with a suitably substituted compound of formula (VII-S), wherein $A^1$ is a suitably selected MgBr, MgCl, and the like, a known compound or compound prepared by known methods; wherein the compound of formula (VII-S) is preferably present in an amount in the range of from about 1.0 to about 3.0 molar equivalents (relative to the moles of the compound of formula (VI-S)), more preferably in an amount in the range of from about 1.25 to about 1.75 molar equivalents;

in a suitably selected anhydrous organic solvent such as THF, 2methyl-THF, MTBE, cyclopentyl methyl ether, and the like, or mixture thereof; preferably a temperature in the range of from about –20° C. to about 0° C.; to yield the corresponding compound of formula (VIII-S), which compound is preferably not isolated.

Alternatively, a suitably substituted compound of formula (VII-S) wherein $A^1$ is a halogen such as Cl, Br, and the like, is treated with n-butyl lithium, and the like; to effect metal-halogen exchange; and the resulting mixture is reacted with the compound of formula (VI-S); wherein the compound of formula (VII-S) is preferably present in an amount in the range of from about 1.0 to about 2.0 molar equivalents (relative to the moles of the compound of formula (VI-S)), more preferably in an amount in the range of from about 1.0 to about 1.2 molar equivalents;

in a suitably selected anhydrous organic solvent such as THF, 2methyl-THF, MTBE, cyclopentyl methyl ether, and the like, or mixture thereof; preferably a temperature in the range of from about –50° C. to about 0° C.; to yield the corresponding compound of formula (VIII-S), which compound is preferably not isolated.

The compound of formula (VIII-S) is reacted with a suitably selected reducing agent such as $Et_3SiH$, sodium borohydride, and the like; wherein the reducing agent is preferably present in an amount in the range of from about 1.0 to about 5.0 molar equivalents (relative to the moles of the compound of formula (VIII-S)), more preferably in an amount in the range of from about 1.0 to about 2.0 molar equivalents;

in the presence of a suitably selected Lewis acid such as $BF_3.Et_2O$, and the like: (preferably, wherein $PG^1$ is acetyl, the Lewis acid is selected to remove the hydroxy group without removing the acetyl protecting groups); wherein the Lewis acid is preferably present in an amount in the range of from about 1.0 to about 3.0 molar equivalents (relative to the moles of the compound of formula (VIII-S)), more preferably in an amount in the range of from about 1.0 to about 1.5 molar equivalents;

in a suitably selected second organic solvent such as DCM, acetonitrile, DCE, MTBE, cyclopentyl methyl ether, and the like, or mixture thereof; preferably, at a temperature in the range of from about –20° C. to about 0° C. (during addition of reagents), followed by warming to room temperature; to yield the corresponding compound of formula (IX-S). Preferably, the compound of formula (IX-S) is purified, according to known methods, for example, by recrystallization from a suitably selected solvent such as ethanol, and the like.

The compound of formula (IX-S) is de-protected according to known methods, to yield the corresponding compound of formula (I-S). For example wherein $PG^1$ is acetyl or benzoyl, the compound of formula (IX-S) is reacted with a suitably selected base such as sodium methoxide, potassium carbonate, and the like, preferably sodium methoxide; in an organic solvent or mixture of organic solvents, such as methanol, THF, ethanol, isopropanol, and the like, preferably in mixture of methanol and THF; to yield the corresponding compound of formula (I-S). The compound of formula (I-S) is preferably isolated according to known methods, for example by solvent evaporation, crystallization, column chromatography, and the like.

One skilled in the art will recognize, that the compound of formula (VIII-S) may alternatively be reacted with a suitably selected second Lewis acid, such as $AlCl_3$, titanium tetrachloride, and the like, which second Lewis acid removes both the hydroxy group and the $PG^1$ protecting groups, simultaneously; wherein the second Lewis acid is preferably present in an amount in the range of from about 1.0 to about 10.0 molar equivalents (relative to the moles of the compound of formula (VIII-S)), more preferably in an amount in the range of from about 1.5 to about 6 molar equivalents;

in a suitably selected third organic solvent such as DCM, acetonitrile, DCE, MTBE, cyclopentyl methyl ether, and the like, or mixture thereof; optionally at a temperature greater than room temperature, preferably at a temperature in the range of from about room temperature to about 65° C.; to yield the corresponding compound of formula (I-S) in a single step. For example, wherein $PG^1$ is acetyl, the compound of formula (VIII-S) may be reacted with $AlCl_3$, to yield the corresponding compound of formula (I-S).

In an embodiment, the present invention is directed to a process for the preparation of a compound of formula (I-T) or a pharmaceutically acceptable salt thereof, as outlined in more detail in Scheme 3.

Scheme 3

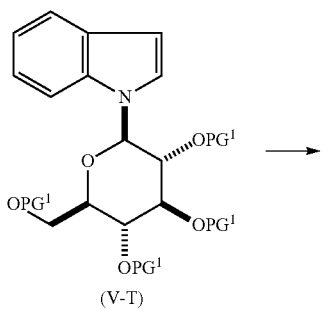

(V-T)

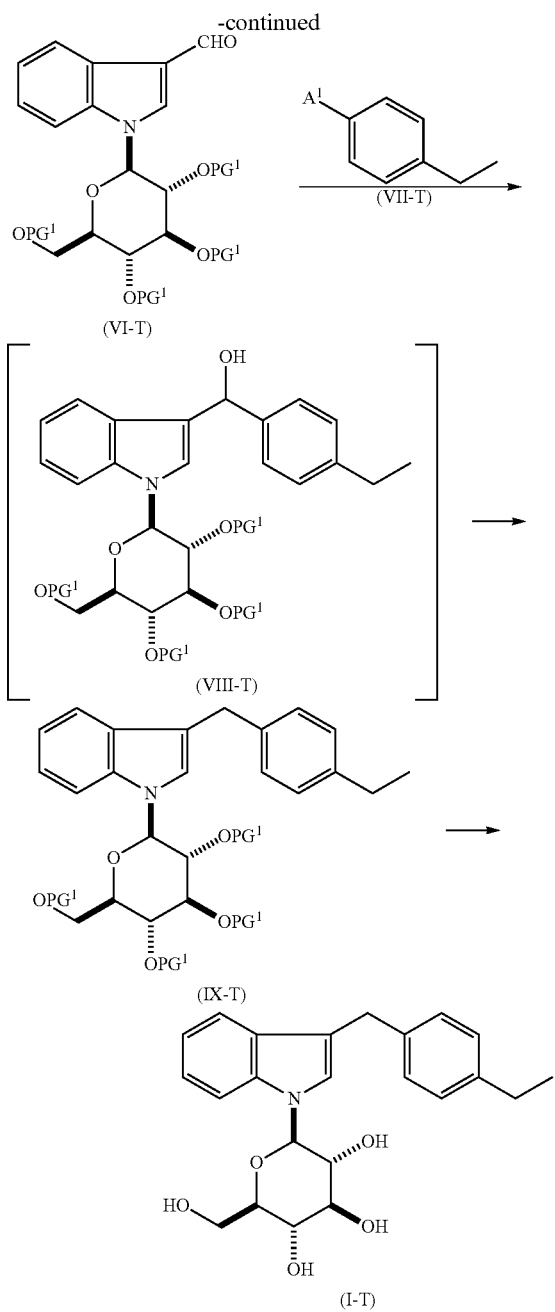

(VI-T)

(VII-T)

(VIII-T)

(IX-T)

(I-T)

Accordingly, a suitably substituted compound of formula (V-T), wherein $PG^1$ is a suitably selected oxygen protecting group, such as acetyl, benzoyl, and the like, preferably acetyl, a known compound or compound prepared by known methods, is reacted with a suitably selected acylating reagent such as phosphoryl chloride, thionyl chloride, oxalyl chloride, and the like; wherein the acylating reagent is preferably present in an amount in the range of from about 1.5 to about 3.0 molar equivalents (relative to the moles of the compound of formula (V-T)), more preferably in an amount in the range of from about 2.0 to about 3.0 molar equivalents;

in the presence of a suitably selected carbonyl source such as DMF, and the like; wherein the carbonyl source is preferably present in an amount in the range of form about 1.0 to about 2.0 molar equivalents (relative to the moles of the compound of formula (V-T)), more preferably in an amount in the range of from about 1.25 to about 1.5 molar equivalents;

in a suitably selected first organic solvent such as DCE, methylene chloride, toluene, chlorobenzene, dichlorobenzene, and the like, or mixture thereof; preferably at a temperature in the range of from about room temperature to about 40° C.; to yield the corresponding compound of formula (VI-T).

Preferably, the reaction mixture resulting from the reaction of the compound of formula (V-T) with the acylating reagent is quenched to remove excess, un-reacted acetylating reagent (particularly when the acylating reagent is phosphoryl chloride), by adding the reaction mixture into a warmed, aqueous sodium acetate or warmed, aqueous potassium acetate solution. Preferably, the reaction mixture is added to a 3M aqueous sodium acetate solution warmed to about 40° C.

The compound of formula (VI-T) is reacted with a suitably substituted compound of formula (VII-T), wherein $A^1$ is a suitably selected MgBr, MgCl, and the like, a known compound or compound prepared by known methods; wherein the compound of formula (VII-T) is preferably present in an amount in the range of from about 1.0 to about 3.0 molar equivalents (relative to the moles of the compound of formula (VI-T)), more preferably in an amount in the range of from about 1.25 to about 1.75 molar equivalents;

in a suitably selected anhydrous organic solvent such as THF, 2methyl-THF, MTBE, cyclopentyl methyl ether, and the like, or mixture thereof; preferably a temperature in the range of from about −20° C. to about 0° C.; to yield the corresponding compound of formula (VIII-T), which compound is preferably not isolated.

Alternatively, a suitably substituted compound of formula (VII-T) wherein $A^1$ is a halogen such as Cl, Br, and the like, is treated with n-butyl lithium, and the like; to effect metal-halogen exchange; and the resulting mixture is reacted with the compound of formula (VI-T); wherein the compound of formula (VII-T) is preferably present in an amount in the range of from about 1.0 to about 2.0 molar equivalents (relative to the moles of the compound of formula (VI-T)), more preferably in an amount in the range of from about 1.0 to about 1.2 molar equivalents;

in a suitably selected anhydrous organic solvent such as THF, 2methyl-THF, MTBE, cyclopentyl methyl ether, and the like, or mixture thereof; preferably a temperature in the range of from about −50° C. to about 0° C.; to yield the corresponding compound of formula (VIII-T), which compound is preferably not isolated.

The compound of formula (VIII-T) is reacted with a suitably selected reducing agent such as $Et_3SiH$, sodium borohydride, and the like; wherein the reducing agent is preferably present in an amount in the range of from about 1.0 to about 5.0 molar equivalents (relative to the moles of the compound of formula (VIII-T)), more preferably in an amount in the range of from about 1.0 to about 2.0 molar equivalents;

in the presence of a suitably selected Lewis acid such as $BF_3.Et_2O$, and the like; (preferably, wherein $PG^1$ is acetyl, the Lewis acid is selected to remove the hydroxy group without removing the acetyl protecting groups); wherein the Lewis acid is preferably present in an amount in the range of from about 1.0 to about 3.0 molar equivalents (relative to the moles of the compound of formula (VIII-T)), more preferably in an amount in the range of from about 1.0 to about 1.5 molar equivalents;

in a suitably selected second organic solvent such as DCM, acetonitrile, DCE, MTBE, cyclopentyl methyl ether, and the like, or mixture thereof; preferably, at a temperature in the range of from about −20° C. to about 0° C. (during addition of reagents), followed by warming to room temperature; to yield the corresponding compound of formula (IX-T). Preferably, the compound of formula (IX-T) is purified, according to known methods, for example, by recrystallization from a suitably selected solvent such as ethanol, and the like.

The compound of formula (IX-T) is de-protected according to known methods, to yield the corresponding compound of formula (I-T). For example wherein PG$^1$ is acetyl or benzoyl, the compound of formula (IX-T) is reacted with a suitably selected base such as sodium methoxide, potassium carbonate, and the like, preferably sodium methoxide; in an organic solvent or mixture of organic solvents, such as methanol, THF, ethanol, isopropanol, and the like, preferably in mixture of methanol and THF; to yield the corresponding compound of formula (I-T). The compound of formula (I-T) is preferably isolated according to known methods, for example by solvent evaporation, crystallization, column chromatography, and the like.

One skilled in the art will recognize, that the compound of formula (VIII-T) may alternatively be reacted with a suitably selected second Lewis acid, such as AlCl$_3$, titanium tetrachloride, and the like, which second Lewis acid removes both the hydroxy group and the PG$^1$ protecting groups, simultaneously; wherein the second Lewis acid is preferably present in an amount in the range of from about 1.0 to about 10, molar equivalents (relative to the moles of the compound of formula (VIII-T)), more preferably in an amount in the range of from about 1.5 to about 6.0 molar equivalents;

in a suitably selected third organic solvent such as DCM, acetonitrile, DCE, MTBE, cyclopentyl methyl ether, and the like, or mixture thereof; optionally at a temperature greater than room temperature, preferably at a temperature in the range of from about room temperature to about 65° C.; to yield the corresponding compound of formula (I-T) in a single step. For example, wherein PG$^1$ is acetyl, the compound of formula (VIII-T) may be reacted with AlCl$_3$, to yield the corresponding compound of formula (I-T).

The present invention is further directed to an improved process for the preparation of a compound of formula (C), Q is selected from the group consisting of $C_{1-4}$alkyl, $C_{3-6}$cycloalkyl, preferably, Q is selected from the group consisting of ethyl and cyclopropyl, as outlined in Scheme 4, below.

Scheme 4

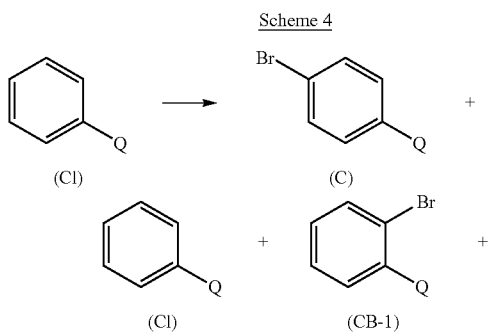

-continued

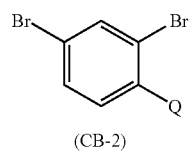

(CB-2)

Accordingly, a suitably substituted compound of formula (CI), wherein Q is as defined above, a known compound or compound prepared by known methods, is reacted with a suitably selected source of bromine, such as Br$_2$, NBS, and the like, preferably Br$_2$; wherein the source of bromine is preferably present in an amount in the range of from about 1.0 to about 2.0 molar equivalents (relative to the moles of the compound of formula (CI)), more preferably, in an amount in the range of from about 1.0 to about 1.25 molar equivalents, more preferably in an amount of about 1.02 molar equivalents;

in a suitably selected organic solvent such as DCM, diethyl ether, and the like, preferably DCM, (preferably, in an organic solvent with a freezing point of lower than about −78° C.); at a temperature in the range of form about −65° C. to about −78° C., preferably at about −76° C.; to yield the corresponding compound of formula (CI), in a mixture with un-reacted starting material, the compound of formula (CI) and un-desired by-products, the compound of formula (CB-1) and the compound of formula (CB-2). Preferably, the source of bromine is added to the compound of formula (CI) at a rate such that the temperature of the reaction mixture is maintained within about 5° C., more preferably within about 2-3° C. Preferably, the desired compound of formula (C) is isolated by distillation.

The preparation of the compound of formula (C) is disclosed by LEVIN, R. Y., et al., in "Bromination and acylatin of phenylcyclopropane", *Zhurmal Obshchei Khimii*, (1961), pp 3480-3481, Vol. 31.

The process of the present invention is improved over the process as disclosed by Levin et al. The process of the present invention (as described above and further in Example 7, which follows herein) yields improved selectivity for the desired brominated species, thereby improving overall yield and resulting in a less complex mixture from which the desired brominated product must be isolated.

Figure 2:
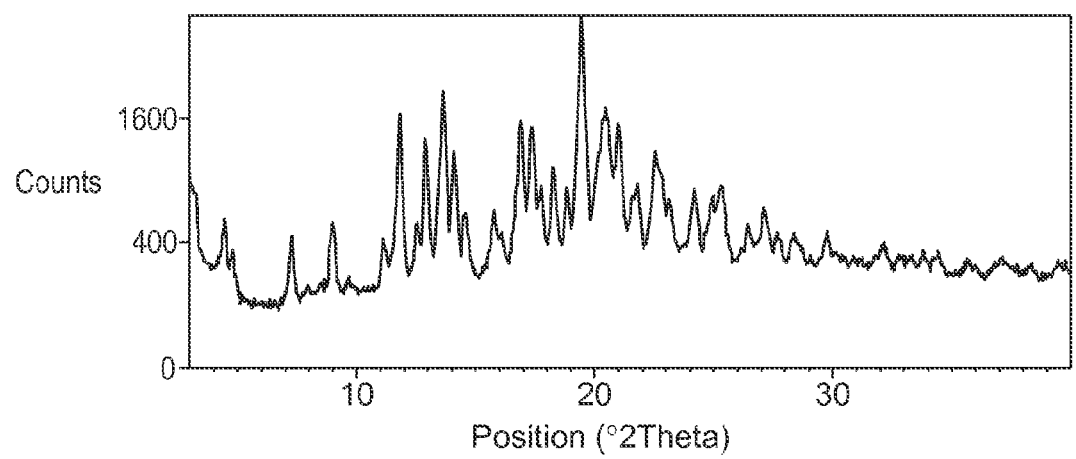
FIG. 2 illustrates a representative pXRD for the crystalline hemihydrate of the compound of formula (I-S).

The present invention is further directed to a crystalline ethanol solvate form of the compound of formula (I-S). FIG. 1, which follows herein, illustrates a representative pXRD spectra for the crystalline ethanolate (ethanol solvate) of the compound of formula (I-S). The present invention is further directed to a crystalline hemi-hydrate form of the compound of formula (I-S). FIG. 2, which follows herein, illustrates a representative pXRD spectra for the crystalline hemihydrate of the compound of formula (I-S).

Figure 3:
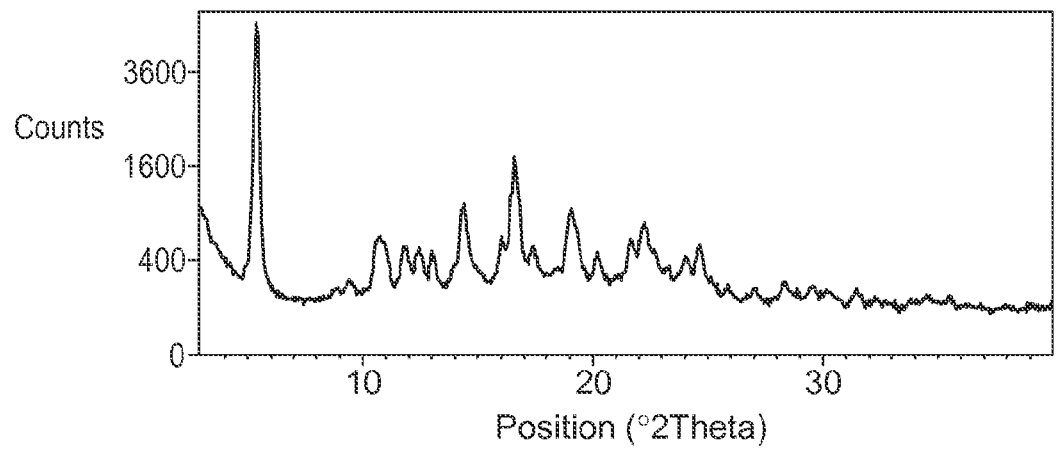
FIG. 3 illustrates a representative pXRD for the crystalline ethanolate (ethanol solvate) of the compound of formula (I-T).
Figure 4:
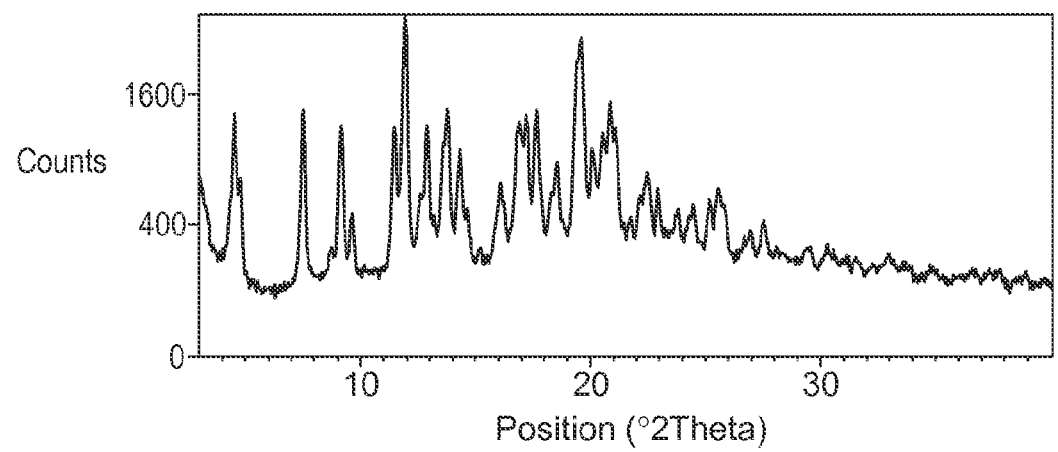
FIG. 4 illustrates a representative pXRD for the crystalline hemihydrate of the compound of formula (I-T).

The present invention is further directed to a crystalline ethanol solvate form of the compound of formula (I-T). FIG. 3, which follows herein, illustrates a representative pXRD spectra for the crystalline ethanolate (ethanol solvate) compound of formula (I-S). The present invention is further directed to a crystalline hemi-hydrate form of the compound of formula (I-T). FIG. 4, which follows herein, illustrates a representative pXRD spectra for the crystalline hemihydrate of the compound of formula (I-T).

The crystalline ethanolate compound of formula (I-S) may be prepared according to the procedure as described in more detail in Example 5, which follows herein; the crystalline hemihydrate compound of formula (I-S) may be prepared according to the procedure as described in more detail in Example 6, which follows herein; the crystalline ethanolate compound of formula (I-T) may be prepared according to the procedure as described in more detail in Example 12, which follows herein; and the crystalline hemihydrate compound of formula (I-T) may be prepared according to the procedure as described in more detail in Example 13, which follows herein.

Powder X-ray diffraction (pXRD) patterns were measured for the crystalline ethanolate compound of formula (I-S), the crystalline ethanolate compound of formula (I-T), the crystalline hemihydrate compound of formula (I-S) and the crystalline hemihydrate compound of formula (I-T) using either a Bruker AXS/Model D8 Advance (equipped with a scintillation detector, parallel beam optics (Goebel Mirrors), and a Cu radiation source or a Philips Panalytical X'Pert diffractometer. The spectra were collected scanning from 3 to 40° in 2θ, at a scan rate of 3° in 2θ/min. The X-ray tube voltage and current settings were 45 KV and 40 mA, respectively. Each sample was packed onto a zero background holder and scanned under ambient conditions of temperature and humidity.

In an embodiment, the present invention is directed to a crystalline ethanolate (ethanol solvate) of the compound of formula (I-S). The crystallinity of the ethanolate compound of formula (I-S) was confirmed by optical birefringence.

In an embodiment, the ethanolate compound of formula (I-S) may be characterized by its corresponding pXRD peaks, as listed in Table 1, below.

TABLE 1 pXRD for Crystalline Ethanolate Compound of Formula (I-S)

| Position [°2θ.] | d-spacing [Å] | Relative Intensity [%] |
|---|---|---|
| 5.58 | 15.83 | 100 |
| 11.18 | 7.91 | 15 |
| 12.54 | 7.06 | 3 |
| 14.50 | 6.11 | 13 |
| 16.82 | 5.27 | 56 |
| 19.20 | 4.62 | 18 |
| 20.27 | 4.38 | 7 |
| 21.69 | 4.10 | 5 |
| 22.37 | 3.97 | 9 |
| 27.02 | 3.30 | 2 |

Preferably, the crystalline ethanolate compound of formula (I-S) may be characterized by its pXRD, wherein the pXRD peaks exhibit a relative intensity of greater than or equal to about 10%.

In another embodiment of the present invention, the crystalline ethanolate compound of formula (I-S) may be characterized by its lower angle pXRD peaks, exhibiting 2°θ of about 5.58, 11.18, 12.54, 14.50, 16.82 and 19.20.

In an embodiment, the hemihydrate compound of formula (I-S) may be characterized by its corresponding pXRD peaks, as listed in Table 2, below.

TABLE 2 pXRD for Crystalline Hemihydrate Compound of Formula (I-S)

| Position [°2θ.] | d-spacing [Å] | Relative Intensity [%] |
|---|---|---|
| 4.51 | 19.59 | 12 |
| 7.32 | 12.05 | 11 |
| 9.02 | 9.80 | 14 |
| 11.87 | 7.46 | 48 |
| 12.54 | 7.06 | 12 |
| 12.91 | 6.86 | 39 |
| 13.68 | 6.47 | 61 |
| 14.13 | 6.27 | 34 |
| 14.58 | 6.08 | 14 |
| 15.88 | 5.58 | 12 |
| 16.94 | 5.23 | 45 |
| 17.41 | 5.09 | 43 |
| 18.28 | 4.85 | 26 |
| 18.86 | 4.71 | 20 |
| 19.47 | 4.56 | 100 |
| 20.62 | 4.31 | 44 |
| 21.03 | 4.22 | 42 |
| 21.86 | 4.06 | 22 |
| 22.57 | 3.94 | 31 |
| 24.24 | 3.67 | 19 |
| 25.39 | 3.51 | 19 |
| 27.17 | 3.28 | 12 |
| 28.49 | 3.13 | 5 |

Preferably, the crystalline hemihydrate compound of formula (I-S) may be characterized by its pXRD, wherein the pXRD peaks exhibit a relative intensity of greater than or equal to about 20%, more preferably, greater than or equal to about 40%.

In another embodiment of the present invention, the crystalline hemihydrate compound of formula (I-S) may be characterized by its low-angle pXRD peaks, exhibiting 2*θ of about 4.51, 7.32, 9.02, 11.87, 12.54 and 12.91.

In an embodiment, the crystalline ethanolate (ethanol solvate) compound of formula (I-T) may be characterized by its corresponding pXRD, as listed in Table 3, below.

TABLE 3 pXRD for Crystalline Ethanolate Compound of Formula (I-T)

| Position [°2θ] | d-spacing [Å] | Relative Intensity [%] |
|---|---|---|
| 5.58 | 15.83 | 100 |
| 9.57 | 9.24 | 2 |
| 10.73 | 8.24 | 3 |
| 11.19 | 7.91 | 15 |
| 12.61 | 7.02 | 3 |
| 14.08 | 6.29 | 2 |
| 14.50 | 6.11 | 12 |
| 16.82 | 5.27 | 56 |
| 19.21 | 4.62 | 18 |
| 20.29 | 4.378 | 7 |
| 21.69 | 4.10 | 5 |
| 22.43 | 3.96 | 8 |
| 23.22 | 3.83 | 2 |
| 24.46 | 3.64 | 0.7 |
| 25.25 | 3.53 | 1 |
| 27.04 | 3.30 | 2 |
| 28.39 | 3.14 | 1 |
| 29.70 | 3.01 | 2 |
| 31.39 | 2.85 | 1 |
| 35.32 | 2.54 | 1 |

Preferably, the crystalline ethanolate compound of formula (I-T) may be characterized by its pXRD, wherein the pXRD peaks exhibit a relative intensity of greater than or equal to about 10%.

In another embodiment of the present invention, the crystalline ethanolate compound of formula (I-T) may be characterized by its lower angle pXRD peaks, exhibiting 2°θ of about 5.58, 11.19, 14.50, 16.82 and 19.21.

In an embodiment, the crystalline hemihydrate compound of formula (I-T) may be characterized by its corresponding pXRD, as listed in Table 4, below.

TABLE 4 pXRD for Crystalline Hemihydrate Compound of Formula (I-T)

| Position [°2θ] | d-spacing [Å] | Relative Intensity [%] |
|---|---|---|
| 4.56 | 19.40 | 46 |
| 7.55 | 11.71 | 49 |
| 9.20 | 9.62 | 39 |
| 9.62 | 9.19 | 13 |
| 11.50 | 7.70 | 40 |
| 11.96 | 7.40 | 100 |
| 12.91 | 6.86 | 39 |
| 13.80 | 6.42 | 46 |
| 14.20 | 6.20 | 33 |
| 16.06 | 5.52 | 21 |
| 16.82 | 5.27 | 41 |
| 17.24 | 5.14 | 43 |
| 17.62 | 5.03 | 47 |
| 18.51 | 4.79 | 27 |
| 19.31 | 4.60 | 66 |
| 19.60 | 4.53 | 79 |
| 20.02 | 4.43 | 32 |
| 20.79 | 4.27 | 52 |
| 21.06 | 4.22 | 38 |
| 22.44 | 3.96 | 22 |
| 22.87 | 3.89 | 18 |
| 24.39 | 3.65 | 12 |
| 25.08 | 3.55 | 14 |
| 25.51 | 3.49 | 18 |

Preferably, the crystalline hemihydrate compound of formula (I-T) may be characterized by its pXRD, wherein the pXRD peaks exhibit a relative intensity of greater than or equal to about 25%, more preferably, greater than or equal to about 40%.

In another embodiment of the present invention, the crystalline hemihydrate compound of formula (I-T) may be characterized by its low-angle pXRD peaks, exhibiting 2°θ of about 4.56, 7.55, 9.20, 9.62, 11.50 and 11.96.

The present invention further comprises pharmaceutical compositions containing a compound prepared according to any of the processes described herein with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein may contain, per unit dosage unit, e.g., tablet, capsule, powder, injection, suppository, teaspoonful and the like, of from about 0.01 to about 1,000 mg or any amount or range therein, preferably about 0.01 mg/kg body weight to about 100 mg/kg body weight, or any amount or range therein, and may be given at a dosage of from about 0.01 to about 300 mg/kg/day, or any amount or range therein; preferably from about 0.1 to about 100 mg/kg/day, or any amount or range therein; more preferably from about 0.01 mg/kg to about 50 mg/kg, or any amount or range therein; more preferably, from about 0.01 mg/kg to about 30 mg/kg, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 1,000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of treating described in the present invention may also be carried out using a pharmaceutical composition comprising any of the compounds as defined herein and a pharmaceutically acceptable carrier. The pharmaceutical composition may contain between about 0.01 mg and about 1,000 mg of the compound, or any amount or range therein; preferably about 1.00 to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations, which generally contain suitable preservatives, are employed when intravenous administration is desired.

To prepare a pharmaceutical composition of the present invention, a compound prepared according to any of the processes described herein as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosaae Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders as described herein is required.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

(2R,3R,4S,5R,6R)-2-(acetoxymethyl)-6-(4-fluoro-3-formyl-1H-indol-1-yl)tetrahydro-2H-pyran-3,4,5-triyl triacetate

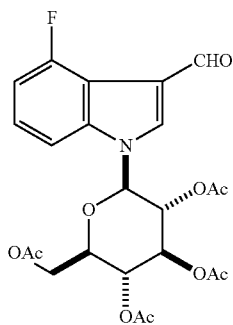

A 5-L 4-neck round bottom flask equipped with a thermocouple controller, mechanical stirrer, addition funnel, condenser, heating mantle, and a nitrogen inlet adapter was (2R,3R,4S,5R,6R)-2-(acetoxymethyl)-6-(4-fluoro-1H-indol-1-yl)tetrahydro-2H-pyran-3,4,5-triyl triacetate (225.0 g, 0.459 mol), DCE (1.5 L) and DMF (50.2 mL, 0.643 mol). The resulting mixture was warmed to 25° C. then phosphoryl chloride (107.8 mL, 1.15 mol) was added slowly via an addition funnel over 75 min. The resulting mixture was stirred for 30 min after the addition was completed, then slowly warmed to 40° C. over 30 min, and then agitated at 40° C. for an additional 12 h. The resulting solution was slowly poured into a rapidly stirred warm (40° C.) 3M aqueous NaOAc (3.0 L) solution over 45 min. After the addition was completed, $CH_2Cl_2$ (4.0 L) was added and the phases were separated. The aqueous phase was back extracted with $CH_2Cl_2$ (1.0 L) and the organic phases were combined, washed with 0.05 M HCl (2.0 L) and deionized water (2.0 L), then dried over $MgSO_4$. After filtration, the solvents were concentrated to dryness in vacuo to yield a solid, which was flushed with ethanol (1.0 L) and re-evaporated. The resulting solid was transferred into a vacuum oven and dried at 40° C. for 20 h to yield the title compound as a slightly yellow-brown solid.

$^1$H NMR (DMSO-$d_6$, 300 MHz) δ 10.1 (s, 1H), 8.53 (s, 1H), 7.66 (d, J=7.3 Hz, 1H), 7.38 (m, 1H), 7.10 (dd, J=6.7, 6.9 Hz, 1H), 6.38 (d, J=7.5 Hz, 1H), 5.68 (dd, J=6.5, 6.6 Hz, 1H), 5.56 (t, J=7.1 Hz, 1H), 5.32 (t, J=7.2 Hz, 1H) 4.41-4.28 (m, 1H), 4.24-4.06 (m, 2H), 2.05 (s, 3H), 2.0 (s, 3H), 1.98 (s, 3H), 1.64 (s, 3H)

$^{13}$C NMR (DMSO-$d_6$, 75.47 MHz) δ183.8, 169.9, 169.5, 169.3, 168.4, 155.8, 139.2, 135.7, 124.8, 117.7, 113.1, 108.3, 107.9, 81.9, 73.5, 72.1, 70.3, 67.6, 61.9, 20.4, 20.3, 20.1, 19.6

LC-MS m/z $MH^+$=494 ($MH^+$), 516 $[M+Na]^+$, 1009 $[2M+Na]^+$ $[α]_D^{25}$=−0.099 (c=0.316, $CHCl_3$).

Example 2

(2R,3R,4S,5R,6R)-2-(acetoxymethyl)-6-(3-((4-cyclopropylphenyl)(hydroxy)methyl)-4-fluoro-1H-indol-1-yl)tetrahydro-2H-pyran-3,4,5-triyl triacetate

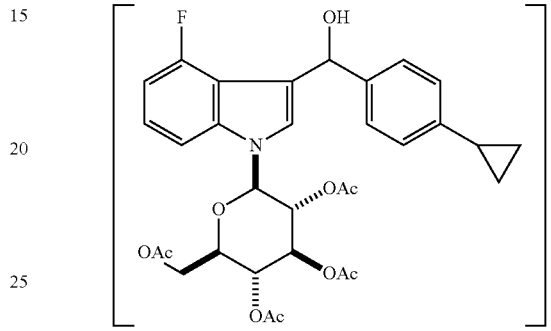

A 12-L 4-neck round bottom flask equipped with a mechanical stirrer, a thermocouple, a septum and nitrogen inlet adapter was charged with the compound prepared as in Example 1 (230 g, 0.457 mol) and anhydrous THF (4.2 L), and the resulting solution was cooled to 0° C. with stirring under $N_2$. A solution of freshly prepared (4-cyclopropylphenyl)magnesium bromide in THF (530 mL) was added dropwise via a double-tipped needle under gentle positive nitrogen pressure over 20 min, while the internal temperature was maintained between 0-8° C. by adjusting the rate of addition. The resulting mixture was stirred at 0° C. for 30 min. The reaction was quenched with saturated aqueous $NH_4Cl$ solution (5.4 L) and then extracted with EtOAc (4 L, 3 L). The combined organic phase was washed with brine (2.7 L) and dried over $MgSO_4$. After filtration, the filtrate was concentrated at 66° C. under house vacuum (~120 mmHg) followed by hi-vacuum (~20 mmHg) to yield a residue which contained a large amount of EtOAc, which residue was chased with $CH_2Cl_2$ (800 mL) to yield the title compound as a yellowish solid, which was used in next step without further purification.

$^1$H NMR (DMSO-$d_6$, 300 MHz) δ 7.53 (dd, J=7.9, 1.1 Hz, 1H), 7.41 (dd, J=8.0, 1.0 Hz, 1H), 7.10-6.92 (m, 3H), 6.78 (m, 1H), 6.15 (m, 1H), 5.92 (dd, J=5.0, 4.1 Hz, 1H), 5.65 (dd, J=5.1, 4.2 Hz, 1H), 5.50 (m, 1H), 5.24 (dd, J=7.9, 8.3 Hz, 1H), 4.38-4.22 (m, 1H), 4.20-4.0 (m, 2H), 2.05 (s, 3H), 2.01 (s, 3H), 1.98 (s, 3H), 1.84 (m, 1H), 0.92 (m, 2H), 0.61 (m, 2H)

$^{13}$C NMR (DMSO-$d_6$, 75.47 MHz): δ170.1, 170.0, 169.9, 169.3, 156.1, 140.9, 139.0, 137.9, 128.0 (2C), 125.2 (2C), 124.2, 122.6, 116.3, 114.6, 107.4, 105.2, 81.5, 76.8, 73.0, 72.6, 70.1, 68.2, 62.0, 20.6, 20.4, 20.2, 19.8, 14.8, 8.96 (2C)

LC-MS m/z $MH^+$=612 ($MH^+$), 634 $[M+Na]^+$.

Example 3

(2R,3R,4S,5R,6R)-2-(acetoxymethyl)-6-(3-(4-cyclopropylbenzyl)-4-fluoro-1H-indol-1-yl)tetrahydro-2H-pyran-3,4,5-triyl triacetate

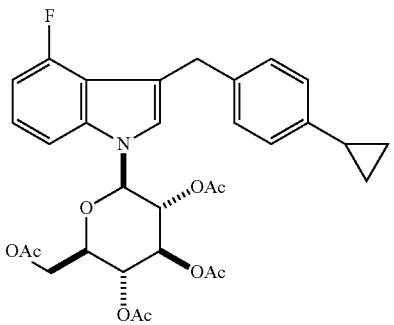

A 3-L 4-neck round bottom flask equipped with a mechanical stirrer, a thermocouple, a septum and nitrogen inlet adapter, was charged with the product prepared as in Example 2 above (82%, 334.6 g, 0.449 mol), DCE (1.14 L), CH$_3$CN (2.28 L), and Et$_3$SiH (108.6 mL, 0.671 mol) and the resulting mixture was stirred and cooled to 0° C. under N$_2$. Boron trifluoride etherate (68.8 mL; 0.539 mol) was added dropwise over 10 min and the resulting mixture was stirred at 0° C. for 30 minutes. After completion, saturated aqueous NaHCO$_3$ solution (4.2 L) was added to the mixture, which was extracted with EtOAc (5 L, 4 L) and the combined organic phase was dried over MgSO$_4$. After filtration, the filtrate was concentrated under house vacuum at 60° C. to yield the title compound as a slightly yellowish solid.

The slightly yellowish solid (315.0 g) was triturated with EtOH (2.1 L, 200 proof) in a 4-L heavy duty Erlenmeyer flask at 76° C. (with sonication×3), and then gradually cooled to 20° C. and stirred under N$_2$ for 1 h. The solid was then collected by filtration and washed with cold (0° C.) EtOH (200 mL), dried by air-suction for 30 min, and then placed in a vacuum oven under house vacuum with gentle of N$_2$ stream at 60° C. for 18 h, to yield the title compound as an off-white crystalline solid.

$^1$H NMR (DMSO-d$_6$, 300 MHz) δ 7.47 (d, J=8.3 Hz, 1H), 7.22 (s, 1H), 7.20-7.10 (m, 1H), 7.06 (d, J=8.1, 2H), 6.95 (d, J=8.1 Hz, 1H), 6.78 (dd, J=7.1, 7.0 Hz, 1H), 6.16 (d, J=7.1 Hz, 1H), 5.61-5.44 (m, 2H), 5.21 (t, J=7.3, 7.1 Hz, 1H), 4.34-4.21 (m, 1H), 4.18-4.04 (m, 2H), 4.0 (s, 2H), 2.04 (s, 3H), 1.97 (s, 3H), 1.95 (s, 3H), 1.84 (m, 1H), 1.63 (s, 3H), 0.89 (m, 2H), 0.61 (m, 2H)

$^{13}$C NMR (DMSO-d$_6$, 75.47 MHz): δ169.9, 169.5, 169.3, 168.3, 156.2, 140.9, 139.0, 137.9, 128.0 (2C), 125.2 (2C), 124.2, 122.7, 116.1, 114.1, 107.2, 105.0, 81.7, 73.0, 72.5, 69.8, 68.0, 62.0, 31.2, 20.4, 20.3, 20.2, 19.7, 14.6, 8.93 (2C)

LC-MS m/z MH$^+$=596 (MH$^+$), 618 [M+Na]$^+$, 1213 [2M+Na]$^+$

[α]$_D^{25}$=−0.008 (c=0.306, CHCl$_3$).

Example 4

(2R,3R,4S,5S,6R)-2-(3-(4-cyclopropylbenzyl)-4-fluoro-1H-indol-1-yl)-6-(hydroxymethyl)tetrahydro-2H-pyran-3,4,5-triol, ethanolate

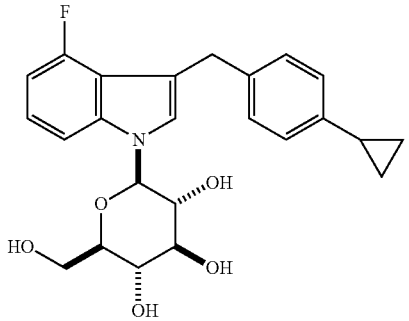

A 12-L 4-neck round bottom flask equipped with a mechanical stirrer, a thermocouple, a septum and nitrogen inlet adapter, was charged with the compound prepared as in Example 3 above (250 g, 0.413 mol), MeOH (1.2 L) and THF (2.4 L), and the resulting mixture was stirred at 20° C. under N$_2$. Sodium methoxide (2.5 mL, 0.012 mol) solution was added dropwise and the resulting mixture was stirred at 20° C. for 3 h. The solvent was concentrated at 60° C. under house vacuum to yield a residue, which was dissolved in EtOAc (8.0 L), washed with brine (800 mL×2) (Note 2), and dried over MgSO$_4$. The insoluble materials were removed by filtration, and the filtrate was concentrated at 60-66° C. under hi-vacuum (20 mmHg) to yield the title compound as a slightly yellowish foamy solid.

The above obtained slightly yellowish foamy solid (195.1 g) was dissolved in EtOH (900 mL) at 76° C., and deionized H$_2$O (1800 mL) was added slowly in a small stream that resulted in a slightly yellowish clear solution, which was then gradually cooled to 40° C. with stirring while seeded (wherein the seeds were prepared, for example, as described in Example 5, below). The resulting slightly white-yellowish suspension was stirred at 20° C. for 20 h, the solids were collected by filtration, washed with cold (0° C.) EtOH/H$_2$O (1:4), and dried by air-suction for 6 h with gentle stream of N$_2$ to yield the title compound as an off-white crystalline solid, as its corresponding EtOH/H$_2$O solvate.

The structure of the EtOH/H$_2$O solvate was confirmed by its $^1$H-NMR and LC-MS analyses. $^1$H-NMR indicated strong H$_2$O and EtOH solvent residues, and the EtOH residue could not be removed by drying process. In addition, p-XRD of this crystalline solid showed a different pattern than that measured for a hemi-hydrate standard.

Example 5

(2R,3R,4S,5S,6R)-2-(3-(4-cyclopropylbenzyl)-4-fluoro-1H-indol-1-yl)-6-(hydroxymethyl)tetrahydro-2H-pyran-3,4,5-triol, ethanolate

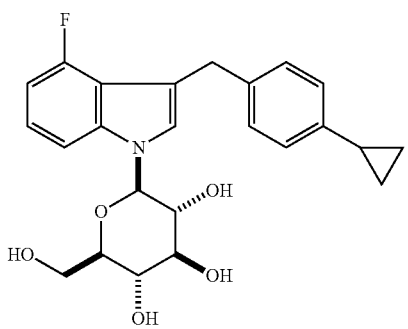

A 500-mL 3-neck round bottom flask equipped with a mechanical stirrer was charged with the compound prepared as in Example 3 above (4.67 g, 0.00784 mol), MeOH (47 mL) and THF (93 mL), and the resulting mixture was stirred at room temperature under argon atmosphere. Sodium methoxide (catalytic amount) solution was added dropwise and the resulting mixture was stirred at room temperature for 1 h. The solvent was concentrated at 30° C. under reduced pressure. The residue was purified by silica gel column chromatography (chloroform:methanol=99:1-90:10) to yield a colorless foamy solid (3.17 g).

First Crystallization

A portion of the colorless foamy solid prepared as described above (0.056 g) was crystallized from EtOH/H$_2$O (1:9, 5 mL), at room temperature, to yield the title compound, as its corresponding EtOH solvate, as colorless crystals (0.047 g).

Second Crystallization

A second portion of the colorless foamy solid prepared as described above (1.21 g) was dissolved in EtOH (6 mL) at room temperature. H$_2$O (6 mL) was added, followed by addition of seeds (the colorless crystals, prepared as described in the first crystallization step above). The resulting suspension was stirred at room temperature for 18 h, the solids were collected by filtration, washed with EtOH/H$_2$O (1:4), and dried under reduced pressure to yield the title compound t, as its corresponding EtOH solvate, as an colorless crystalline solid (0.856 g).

The structure for the isolated compound was confirmed by $^1$H NMR, with peaks corresponding to the compound of formula (I-S) plus ethanol.

Example 6

(2R,3R,4S,5S,6R)-2-(3-(4-cyclopropylbenzyl-4-fluoro-1H-indol-1-yl)-6-(hydroxymethyl)tetrahydro-2H-pyran-3,4,5-triol hemihydrate

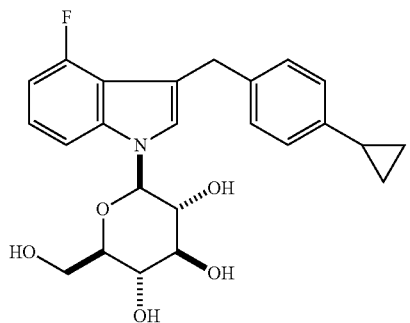

A 5-L 4-neck round bottom flask equipped with a mechanical stirrer, a thermocouple, a septum and nitrogen inlet adapter was charged with the ethanolate (solvate) compound prepared as in Example 4 above (198.5 g, 0.399 mol) and deionized H$_2$O (3.2 L). After the off-white suspension was warmed to 76° C. in a hot water bath, along with sonication (×4), it was gradually cooled to 20° C. The white suspension was stirred for 20 h at 20° C. and then at 10° C. for 1 h. The solid was collected by filtration, washed with deionized H$_2$O (100 mL×2), dried by air-suction for 2 h. and then placed in an oven under house vacuum with gentle stream of N$_2$ at 50° C. for 20 h, then at 60° C. for 3 h to yield the title compound as an off-white crystalline solid.

$^1$H NMR showed no EtOH residue and the p-XRD confirmed that the isolated material was a crystalline solid. TGA and DSC indicated that the isolated material contained about 2.3% of water (H$_2$O). M.P.=108-111° C.

$^1$H NMR (DMSO-d$_6$, 300 MHz) δ 7.36 (d, J=8.2 Hz, 1H), 7.22 (s, 1H), 7.14 (d, J=8.1, 2H), 7.10-7.0 (m, 1H), 6.96 (d, J=8.1 Hz, 2H), 6.73 (dd, J=7.5, 7.7 Hz, 1H), 5.38 (d, J=7.7 Hz, 1H), 5.21 (d, J=6.9 Hz, 1H), 5.18 (d, J=6.8 Hz, 1H), 5.10 (d, J=6.9 Hz, 1H), 4.54 (t, J=6.9, 1.8 Hz, 1H), 4.04 (s, 2H), 3.75-3.60 (m, 2H), 3.52-3.30 (m, 3H), 3.20-3.17 (m, 1H), 1.84 (m, 1H), 0.89 (m, 2H), 0.61 (m, 2H)

$^{13}$C NMR (DMSO-d$_6$, 75.47 MHz): 6156.2, 140.8, 139.4, 138.2, 128.2 (2C), 125.2 (2C), 124.4, 121.8, 115.9, 112.8, 107.4, 104.2, 84.8, 79.3, 77.4, 71.7, 69.8, 60.8, 31.3, 14.6, 8.92 (2C)

LC-MS m/z MH$^+$=428 (MH$^+$), 450 [M+Na]$^+$, 877 [2M+Na]$^+$

[α]$_D^{25}$=−0.026 (c=0.302, CH$_3$OH)

Elemental Analysis: C$_{24}$H$_{25}$NFO$_5$+0.54H$_2$O (MW=437.20):

Theory: % C, 65.93; % H, 6.24: % N, 3.20; % F, 4.35, % H$_2$O, %2.23.

Found: % C, 65.66; % H, 6.16; % N, 3.05; % F, 4.18, % H$_2$O, %2.26.

Example 7

4-bromocyclopropylbenzene

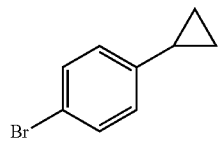

A 12-L 4-neck round bottom flask equipped with a mechanical stirrer, a thermocouple, a dropping funnel, and nitrogen inlet adapter was charged with cyclopropylbenzene (150.0 g, 1.23 mol) and CH$_2$Cl$_2$ (1.5 L). The resulting solution was cooled to −76° C. with stirring. Bromine (65.4 mL, 1.26 mol) in CH$_2$Cl$_2$ (0.75 L) was added slowly dropwise over a 2-h period and the resulting mixture was stirred at −76° C. for 3 h. The resulting mixture was then warmed to −20° C. (in an ice-water bath), saturated aqueous NaHCO$_3$ solution (2.0 L) was added and the mixture was stirred for 10 min. After phase separation, the organic phase was washed with brine (1.0 L) and concentrated at 40° C. under house vacuum (then 20 mmHg for 2 min) to yield a mixture of A:4-bromocyclopropylbenzene; B:2-bromocyclopropylbenzene; C:2,4-dibromocyclopropylbenzene; and D:cyclorporpylbenzene.

The mixture was purified by distillation with a short-path distillation head and KNF Diaphragm pump, to yield the following four fractions under the given conditions. Fractions F2 and F3 were used for the preparation of Gringard reagent as described in Example 8 which follows.

| Fraction | Collection Conditions (head temp ° C./pot temp ° C./mmHg) | A/B/C/D (HPLC area %) | Physical Form |
|---|---|---|---|
| F1 | 30-55° C./80-90° C./6 mm Hg | 26/0.0/0/3/74 | A colorless oil. |
| F2 | 70-80° C./91-100° C./5-6 mm Hg | 93/0.0/1.9/5.1 | A colorless oil |
| F3 | 80-60° C./100-110° C./5-6 mm Hg | 96/0.0/3.6/0.0 | A colorless oil |

-continued

| Fraction | Collection Conditions (head temp ° C./pot temp ° C./mmHg) | A/B/C/D (HPLC area %) | Physical Form |
|---|---|---|---|
| PT | 0° C./>110° C./ 5-6 mm Hg | 15/31/51(?)/0.0 | A yellowish oil |

$^{1}$H NMR (DMSO-$d_6$, 300 MHz) δ 7.48 (d, J=7.9 Hz, 2H), 6.97 (d, J=8.0 Hz, 2H), 1.85 (m, 1H), 0.94 (m, 2H), 0.62 (m, 2H)

$^{13}$C NMR (DMSO-$d_6$, 75.47 MHz) δ143.1, 130.9 (2C), 127.4 (2C), 118.0, 14.6, 9.42 (2C)

LC-MS m/z MH$^+$=197, 199 (MH$^+$).

Example 8

(4-cyclopropylphenyl)magnesium bromide

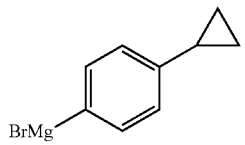

A 2-L 4-neck round bottom flask equipped with a stirrer bar, a thermocouple, a septum and nitrogen inlet adapter was charged with magnesium (17.8 g, 0.725 mol) and stirred at 20° C. Fresh anhydrous THF (420 mL) was added and the resulting suspension was vigorously stirred at 20° C. A solution of 1,2-dibromoethane (0.53 mL, 6.1 mmol) and the two fractions collected in Example 7 above (142.1 g, 0.685 mol) in THF (110 mL) was added dropwise over 20 min at 20° C. under nitrogen atmosphere. When the temperature was 26° C., the resulting mixture was placed in a cold-water bath and the temperature continued to increase to 32° C. gradually. Ice was added to the water bath to maintain the temperature between 40-48° C. with vigorous stirring. When the reaction temperature declined to 16° C., the water bath was removed, and the resulting mixture was stirred at 20° C. for an additional 10-20 min to yield the title compound as a gray-yellowish solution, which was used immediately.

Example 9

(2R,3R,4S,5R,6R)-2-(acetoxymethyl-6-(3-formyl-1H-indol-1-yl)tetrahydro-2H-pyran-3,4,5-triyl triacetate

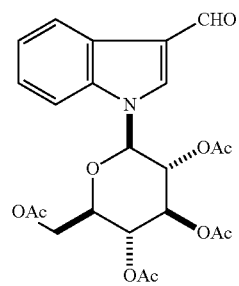

Following the procedure as described in Example 1, above, a mixture of (2R,3R,4S,5R,6R)-2-(acetoxymethyl)-6-(1H-indol-1-yl)tetrahydro-2H-pyran-3,4,5-triyl triacetate (275.0 g, 0.58 mol), DCE (1.83 L) and DMF (63.8 mL, 0.82 mol) at 25° C., was reacted with phosphoryl chloride (137.0 mL, 1.46 mol) to yield the title compound as a slightly yellow-brown solid.

$^{1}$H NMR (DMSO-$d_6$, 300 MHz) δ 9.97 (s, 1H), 8.51 (s, 1H), 8.11 (d, J=7.6 Hz, 1H), 7.80 (d, J=8.3 Hz, 1H), 7.39 (dt. J=7.6 and 1.1 Hz, 1H), 7.30 (t, J=7.5, 1H), 6.35 (d, J=9.0 Hz, 1H), 5.62 (dt, J=25.9 and 9.4 Hz, 2H), 5.31 (t, J=9.9 Hz, 1H), 4.39-4.33 (m, 1H), 4.21-4.11 (m, 2H), 2.06 (s, 3H), 2.00 (s, 3H), 1.98 (s, 3H), 1.64 (s, 3H)

$^{13}$C NMR (DMSO-$d_6$, 125 MHz) δ 185.4, 170.0, 169.5, 169.3, 168.4, 138.1, 136.7, 124.4, 124.1, 123.1, 121.2, 118.8, 111.3, 81.8, 73.4, 72.3, 70.2, 67.8, 62.0, 20.4, 20.3, 20.1, 19.7

Elemental Analysis Calculated for $C_{23}H_{25}NO_{10}$·0.1 mol $H_2O$: C, 57.91; H, 5.32; N, 2.94; KF=0.1%, Measured: C, 57.63; H, 5.44; N, 2.90. KF=0.1%

$[α]_D^{25}$=−37.9 (c=1.0, DMSO).

Example 10

(2R,3R,4S,5R,6S)-2-(acetoxymethyl-6-(3-((4-ethylphenyl)(hydroxy)methyl)-1H-indol-1-yl)tetrahydro-2H-pyran-3,4,5-triyl triacetate

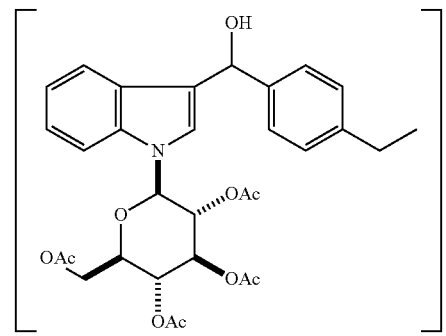

Following the procedure as described in Example 2, above, the compound prepared as in Example 9 above (250 g, 0.526 mol) and anhydrous THF (3.75 L) was reacted with 0.5M 4-ethylbenzene magnesium bromide in THF (1.49 L, 0.747 mol) to yield the title compound as a yellowish solid, which was used directly in the next step without further purification.

$^{1}$H NMR (DMSO-$d_6$, 600.13 MHz) δ 7.59 (dd, J=8.3 and 0.7 Hz, 1H), 7.41 (dd, J=8.0 and 0.9 Hz, 1H), 7.29 (d, J=8.0 Hz, 2H), 7.24 (s, 1H), 7.15-7.12 (m, 1H), 7.12 (d, J=8.3 Hz, 2H), 7.01-6.94 (m, 1H), 6.15 (d, J=9.0 Hz, 1H), 5.87-5.84 (m, 1H), 5.65-5.48 (m, 3H), 5.25-5.19 (m, 1H), 4.31-4.26 (m, 1H), 4.17-4.04 (m, 2H), 2.56 (q, J=7.5 Hz, 2H), 2.04 (s, 3H), 1.98 (s, 3H), 1.96 (s, 3H), 1.64 (s, 3H), 1.15 (t, J=7.6 Hz, 3H)

$^{13}$C NMR (DMSO-$d_6$, 150.92 MHz): δ 169.9, 169.5, 169.3, 162.2, 142.4, 141.8, 136.5, 127.1, 126.4, 126.2, 122.8, 121.8, 121.2, 120.2, 120.1, 119.8, 119.6, 110.5, 81.4, 72.9, 72.6, 69.5, 68.3, 68.0, 62.0, 27.7, 20.4, 20.3, 20.2, 19.8, 15.5

Elemental Analysis for $C_{31}H_{35}NO_{10}$:
Calculated: C, 64.02; H, 6.07; N, 2.41
Measured: C, 64.26; H, 6.30; N, 2.70
$[α]_D^{25}$=−5.6 (c=1.07, DMSO).

Example 11

(2R,3R,4S,5R,6S)-2-(acetoxymethyl)-6-(3-(4-ethyl-benzyl)-1H-indol-1-yl)tetrahydro-2H-pyran-3,4,5-triyl triacetate

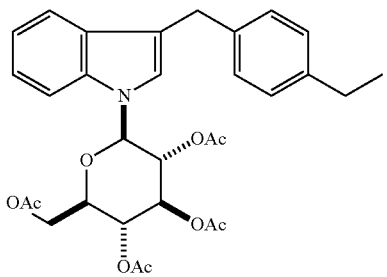

Following the procedure to as described in Example 3, above, a mixture of the compound prepared in Example 10, above (40.0 g, 0.068 mol), DCE (165 mL), MeCN (240 mL), and Et$_3$SiH (16.5 mL, 0.10 mol) was reacted with boron trifluoride etherate (10.44 mL: 0.083 mol) to yield a residue. The residue (40.0 g) was slurried with EtOH (100 mL) at 40° C. and then gradually cooled to 20° C. and stirred for 1 h. The solid was collected by filtration and washed with cold (0° C.) EtOH (25 mL), and then dried to yield the title compound as a white crystalline solid.

$^1$H NMR (DMSO-d$_6$, 300 MHz) δ 7.61 (d, J=8.3 Hz, 1H), 7.41 (d, J=7.9 Hz, 1H), 7.30 (s, 1H), 7.20-7.07 (m, 5H), 7.01 (t, J=7.3 Hz, 1H), 6.16 (d. J=8.6 Hz, 1H), 5.60-5.49 (m, 2H), 5.21 (t, J=9.6 Hz, 1H), 4.33-4.05 (m, 2H), 3.96 (s, 3H), 2.57-2.49 (m, 2H), 2.04 (s, 3H), 1.98 (s, 3H), 1.96 (s, 3H), 1.62 (s, 3H), 1.12 (t, J=7.7 Hz, 3H)

$^{13}$C NMR (DMSO-d$_6$, 75.0 MHz): 169.9, 169.5, 169.2, 168.3, 141.0, 138.0, 136.3, 128.2 (2C), 127.8, 127.4 (2C), 123.3, 121.8, 119.7, 119.0, 115.9, 110.4, 81.4, 72.9, 72.6, 69.8, 68.1, 62.0, 30.2, 27.6, 20.4, 20.3, 20.2, 19.7, 15.5

Elemental Analysis for C$_{31}$H$_{35}$NO$_9$:
Calculated: C, 65.83; H, 6.24; N, 2.48
Measured: C, 65.60; H, 6.16; N, 2.34
$[α]^{25C}$589 nm=−0.49 (10.2 mg/1 mL) DMSO.

Example 12

(2S,3R,4S,5S,6R)-2-(3-(4-ethylbenzyl-1H-indol-1-yl)-6-(hydroxymethyl)tetrahydro-2H-pyran-3,4,5-triol, ethanolate

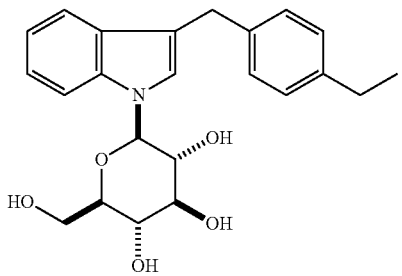

To a solution of the compound prepared as in Example 11 above (30.0 g, 53.0 mmol) in MeOH (0.15 L) and THF (0.3 L) was added sodium methoxide (0.36 mL, 1.6 mmol) and the resulting mixture was stirred at 20° C. for 2 h. The resulting solution was then concentrated to yield an amorphous residue. The amorphous residue was slurried in EtOH (80 mL) and the resulting white suspension was stirred at 20° C. for 2 h. The resulting solids were collected by filtration, washed with cold EtOH, and dried to yield the title compound, as its corresponding EtOH solvate, as a white crystalline solid.

$^1$H NMR (DMSO-d$_6$, 300 MHz) δ 7.50 (d, J=8.2 Hz, 1H), 7.44 (d, J=7.7 Hz, 1H), 7.24-7.20 (m, 3H), 7.13-7.08 (t, J=7.3 Hz, 1H), 5.37 (d, J=9.1 Hz, 2H), 5.19-5.16 (m, 2H), 5.09 (d, J=5.4 Hz, 1H), 4.53 (t, J=5.4 Hz, 1H), 4.37 (t, J=5.2 Hz, 1H), 3.74-3.65 (m, 2H), 3.47-3.36 (m, 5H), 3.28-3.21 (m, 1H), 2.54 (q, J=7.6 Hz, 2H), 2.50-2.48 (m, 1H), 1.13 (t, J=7.6 Hz, 3H), 1.06 (t, J=6.9 Hz, 3H)

$^{13}$C NMR (DMSO-d$_6$, 75.0 MHz): 140.9, 138.3, 136.6, 128.3, 127.8, 127.4, 123.6, 121.4, 119.0, 118.6, 114.5, 10.6, 84.5, 79.2, 77.5, 71.7, 69.9, 60.8, 55.9, 30.4, 27.6, 18.4, 15.5

Elemental Analysis for C$_{23}$H$_{27}$NO$_5$EtOH:
Calculated: C, 67.70; H, 7.50; N, 3.16
Measured: C, 67.34; H, 7.70; N, 3.45
$[α]_D^{25}$=−2.9 (c=1.03, DMSO).

Example 13

(2S,3R,4S,5S,6R)-2-(3-(4-ethylbenzyl)-1H-indol-1-yl)-6-(hydroxymethyl)tetrahydro-2H-pyran-3,4,5-triol, Hemihydrate

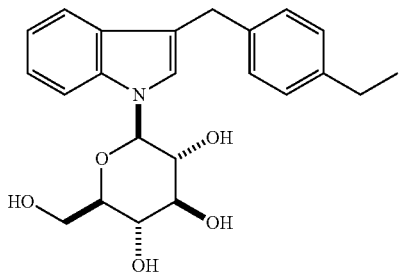

The (2S,3R,4S,5S,6R)-2-(3-(4-ethylbenzyl)-1H-indol-1-yl)-6-(hydroxymethyl)tetrahydro-2H-pyran-3,4,5-triol ethanolate (15.0 g, prepared for example, as described in Example 12, above), was transferred to a 4-neck 1 L round bottom flask equipped with an overhead stirrer, thermocouple, reflux condenser, and a N$_2$ adaptor. To the flask was then added water (375 mL) and the resulting mixture heated to 66° C. The solution became cloudy and eventually the entire solid dissolved. The resulting mixture was then allowed to cool at room temperature overnight. The resultant white slurry contained some large chunks. These chunks were broken up with a spatula and sonicated. The resulting mixture was again stirred at room temperature. The solid material was filtered and rinsed with water (2×50 mL), then dried by suction over 72 h with a N$_2$ bleed over the solid to yield the title compound, (2S,3R,4S,5S,6R)-2-(3-(4-ethylbenzyl)-1H-indol-1-yl)-6-(hydroxymethyl)tetrahydro-2H-pyran-3,4,5-triol hemihydrate as a solid.

The structure for the isolated compound was confirmed by $^1$H NMR, with peaks corresponding to the compound of formula (I-T) plus water.

Example 14

(2S,3R,4S,5S,6R)-2-(3-(4-ethylbenzyl)-1H-indol-1-yl)-6-(hydroxymethyl)tetrahydro-2H-pyran-3,4,5-triol, Hemihydrate

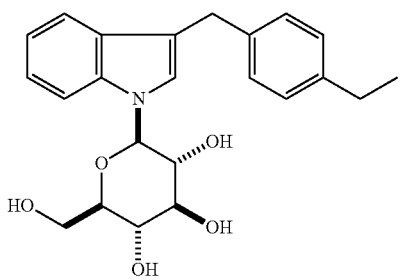

To a 2-L 4-neck round bottom flask equipped with thermocouple controller, $N_2$ inlet/outlet adapter, reflux condenser, and an overhead mechanical stirrer was charged with the compound prepared as in Example 6, above (48.6 g, 0.11 mol) and water (1.2 L). The resulting mixture was heated to 66° C. and the solution became cloudy, but no solid was present. The heating mantle was removed, the cloudy mixture was seeded with the desired hemihydrate crystals (50 mg) (prepared for example as described in Example 13, above), and cooled to room temperature overnight. A white slurry formed overnight with some big chunks of solid visible. The flask was sonicated, the aggregates were broken up with a spatula, and the slurry was stirred an additional 2 h at room temperature. The resulting white slurry was stirred for 6 days for complete the transformation to the hemihydrate. (The conversion was monitored by pXRD.) The resulting mixture was filtered and rinsed with water (2×100 mL). The residue was dried by suction over 72 h with a $N_2$ bleed over the solid to yield the title compound as a white solid.

The structure for the isolated compound was confirmed by $^1$H NMR, with peaks corresponding to the compound of formula (I-T) plus water.

Example 15

Solid, Oral Dosage Form

Prophetic Example

As a specific embodiment of an oral composition, 10 mg of the compound prepared as in Example 6 is formulated with sufficient finely divided lactose to provide a total amount of 580 to 590 mg to fill a size O hard gel capsule.

Example 16

Solid, Oral Dosage Form

Prophetic Example

As a specific embodiment of an oral composition, 10 mg of the compound prepared as in Example 13 or Example 14 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A process for the preparation of a compound of formula (I-S)

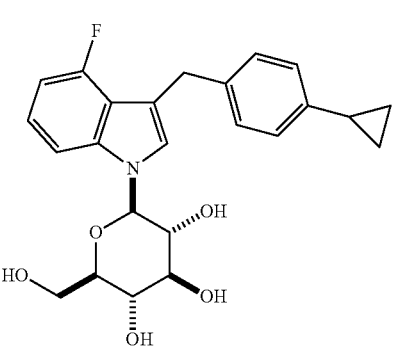

or a pharmaceutically acceptable salt or prodrug thereof; comprising

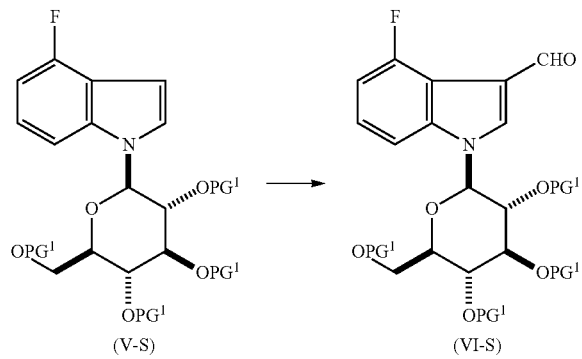

reacting a compound of formula (V-S), wherein $PG^1$ is an oxygen protecting group with an acylating reagent; wherein the acylating reagent is present in an amount in the range of from about 1.5 to 3.0 molar equivalents; in the presence of a carbonyl source; in a first organic solvent; at a temperature in the range of from about room temperature to about 40° C.; to yield the corresponding compound of formula (VI-S);

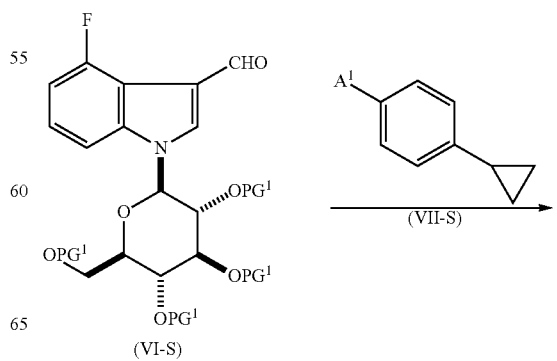

-continued

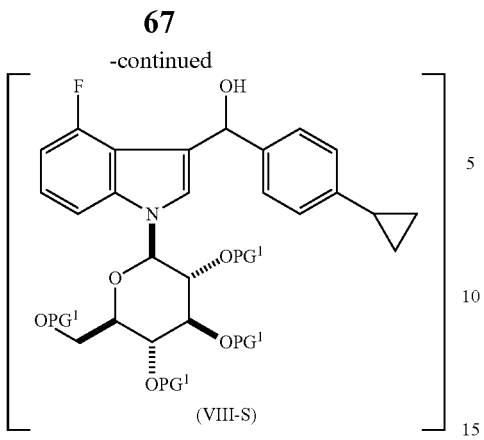

(VIII-S)

reacting the compound of formula (VI-S) with a compound of formula (VII-S), wherein $A^1$ is MgBr or MgCl; in an anhydrous organic solvent; to yield the corresponding compound of formula (VIII-S);

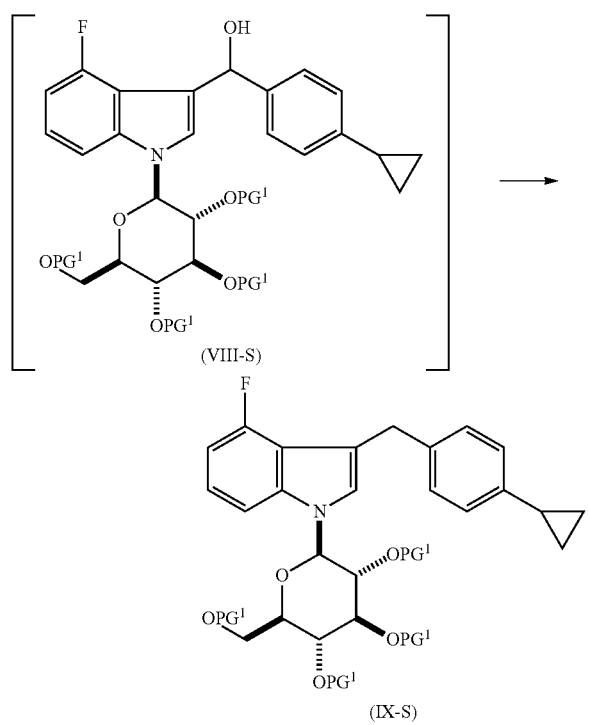

(VIII-S)

(IX-S)

reacting the compound of formula (VIII-S) with a reducing agent; in the presence of a Lewis acid; in a second organic solvent; to yield the corresponding compound of formula (IX-S);

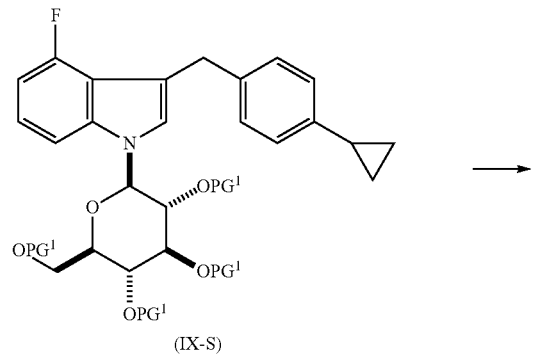

(IX-S)

-continued

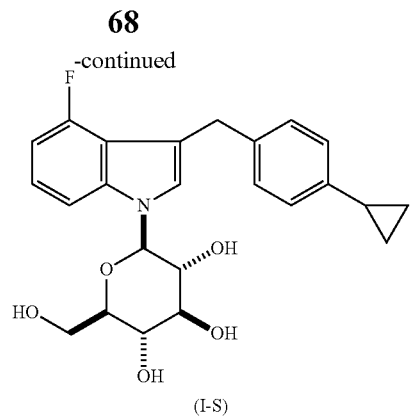

(I-S)

de-protecting the compound of formula (IX-S); to yield the corresponding compound of formula (I-S).

2. The process as in claim 1, wherein $PG^1$ is acetyl.

3. The process as in claim 1, wherein the acylating reagent is phosphoryl chloride, the carbonyl source is N,N-dimethylformamide and the first organic solvent is dichloroethane.

4. The process as in claim 1, further comprising quenching any excess acylating reagent by adding the reaction mixture prepared by reacting the compound of formula (V-S) with the acylating reagent into a warmed, aqueous sodium acetate solution or a warmed, aqueous potassium acetate solution.

5. The process as in claim 4, wherein the reaction mixture prepared by reacting the compound of formula (V-S) with the acylating reagent is added to a 3M aqueous sodium acetate solution warmed to about 40° C.

6. The process as in claim 1, wherein $A^1$ is MgBr and the anhydrous organic solvent is tetrahydrofuran.

7. The process as in claim 6, wherein the compound of formula (VI-S) is reacted with the compound of formula (VII-S) at a temperature in the range of from about −20° C. to about 0° C.

8. The process as in claim 1, wherein the reducing agent is triethylsilane, the Lewis acid is $BF_3$.etherate and the second organic solvent is a mixture of acetonitrile and dichloroethane.

9. The process as in claim 8, wherein the compound of formula (VIII-S) is reacted at a temperature in the range of from about −20° C. to about 0° C.

10. The process as in claim 1, wherein $PG^1$ is acetyl; and wherein the compound of formula (IX-S) is deprotected by reacting the compound of formula (IX-S) with sodium methoxide.

11. A process for the preparation of a compound of formula (I-T)

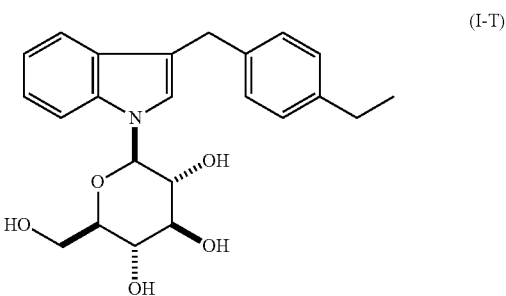 [SMILES: CCc1ccc(Cc2cn([C@@H]3O[C@H](CO)[C@@H](O)[C@H](O)[C@H]3O)c3ccccc23)cc1]

(I-T)

or a pharmaceutically acceptable salt or prodrug thereof;

comprising

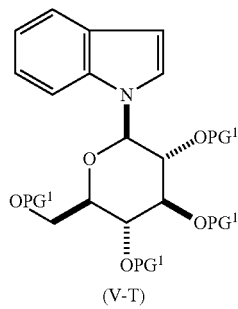

(V-T)

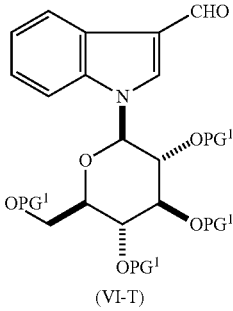

(VI-T)

reacting a compound of formula (V-T), wherein PG¹ is an oxygen protecting group with an acylating reagent; wherein the acylating reagent is present in an amount in the range of from about 1.5 to 3.0 molar equivalents; in the presence of a carbonyl source; in a first organic solvent; at a temperature in the range of from about room temperature to about 40° C.; to yield the corresponding compound of formula (VI-T);

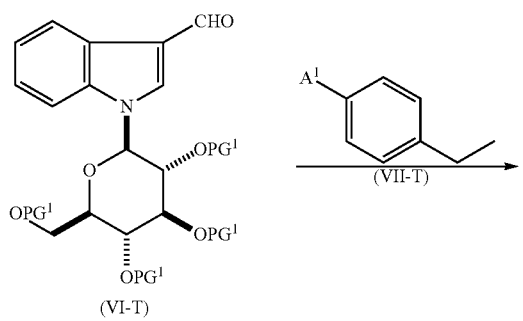
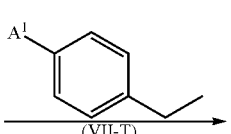

(VI-T)                    (VII-T)

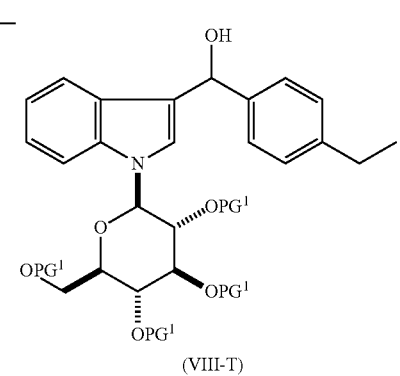

(VIII-T)

reacting the compound of formula (VI-T) with a compound of formula (VII-T), wherein A¹ is MgBr or MgCl; in an anhydrous organic solvent; to yield the corresponding compound of formula (VIII-T);

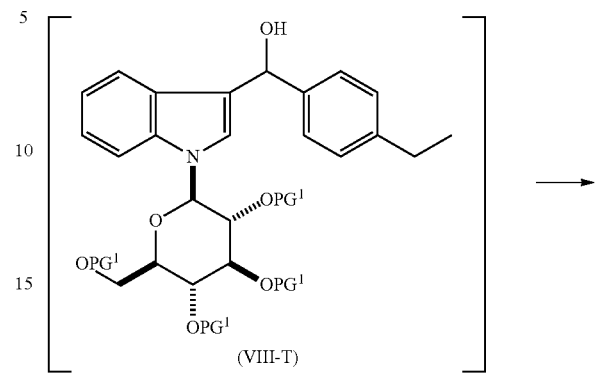

(VIII-T)

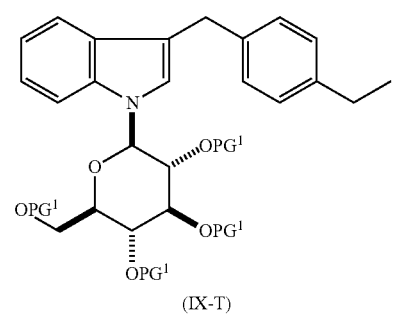

(IX-T)

reacting the compound of formula (VIII-T) with a reducing agent; in the presence of a Lewis acid; in a second organic solvent; to yield the corresponding compound of formula (IX-T);

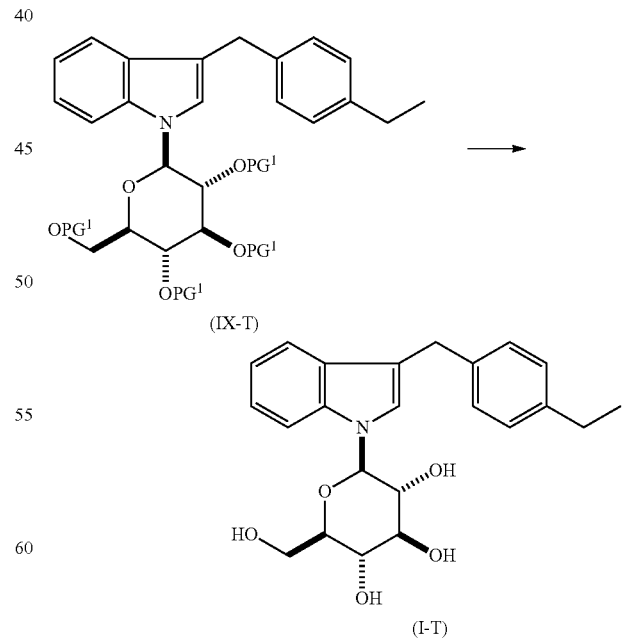

(IX-T)

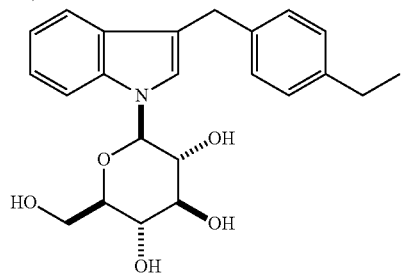

(I-T)

de-protecting the compound of formula (IX-T); to yield the corresponding compound of formula (I-T).

12. The process as in claim 11, wherein $PG^1$ is acetyl.

13. The process as in claim 11, wherein the acylating reagent is phosphoryl chloride, the carbonyl source is N,N-dimethylformamide and the first organic solvent is dichloroethane.

14. The process as in claim 11, further comprising quenching any excess acylating reagent by adding the reaction mixture prepared by reacting the compound of formula (V-T) with the acylating reagent into a warmed, aqueous sodium acetate solution or a warmed, aqueous potassium acetate solution.

15. The process as in claim 14, wherein the reaction mixture prepared by reacting the compound of formula (V-T) with the acylating reagent is added to a 3M aqueous sodium acetate solution warmed to about 40° C.

16. The process as in claim 11, wherein $A^1$ is MgBr and the anhydrous organic solvent is tetrahydrofuran.

17. The process as in claim 16, wherein the compound of formula (VI-T) is reacted with the compound of formula (VII-T) at a temperature in the range of from about −20° C. to about 0° C.

18. The process as in claim 11, wherein the reducing agent is triethylsilane, the Lewis acid is $BF_3$.etherate and the second organic solvent is a mixture of acetonitrile and dichloroethane.

19. The process as in claim 18, wherein the compound of formula (VIII-T) is reacted at a temperature in the range of from about −20° C. to about 0° C.

20. The process as in claim 11, wherein $PG^1$ is acetyl; and wherein the compound of formula (IX-S) is deprotected by reacting the compound of formula (IX-S) with sodium methoxide.

\* \* \* \* \*